(12) United States Patent
Waldmann et al.

(10) Patent No.: US 6,569,430 B1
(45) Date of Patent: *May 27, 2003

(54) ANTIBODIES TO THE ANTIGEN CAMPATH-1

(75) Inventors: Herman Waldmann, Cambridge (GB); Michael R. Clark, Cambridge (GB); Gregory P. Winter, Cambridge (GB); Lutz Riechmann, La Jolla, CA (US)

(73) Assignee: BTG International Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 08/407,620

(22) Filed: Mar. 21, 1995

Related U.S. Application Data

(62) Division of application No. 08/235,705, filed on Apr. 29, 1994, now Pat. No. 5,846,534, which is a continuation of application No. 08/099,480, filed on Jul. 30, 1993, now abandoned, which is a continuation of application No. 07/921,601, filed on Aug. 3, 1992, now abandoned, which is a continuation of application No. 07/424,233, filed on Oct. 12, 1989, now abandoned.

(30) Foreign Application Priority Data

Feb. 12, 1988 (GB) ............................................. 8803228
Feb. 25, 1988 (GB) ............................................. 8804464

(51) Int. Cl.$^7$ .................. A61K 39/395; C12P 21/04; C07H 21/04
(52) U.S. Cl. ............................ 424/133.1; 424/135.1; 424/154.1; 424/155.1; 424/156.1; 435/69.6; 435/328; 530/387.3; 536/23.53
(58) Field of Search ............................ 424/133.1, 135.1, 424/154.1, 155.1, 156.1, 93.1, 93.21; 435/69.6, 69.7, 70.21, 172.2, 172.3, 252.3, 252.33, 320.1, 328, 449, 451, 452; 530/387.3, 387.7, 388.75, 388.8, 388.85, 389.6; 536/23.53

(56) References Cited

U.S. PATENT DOCUMENTS

| | | | | |
|---|---|---|---|---|
| 4,816,567 A | | 3/1989 | Cabilly et al. ............ | 530/387.3 |
| 5,225,539 A | | 7/1993 | Winter .................... | 530/387.3 |
| 5,846,534 A | * | 12/1998 | Waldmann et al. ....... | 424/133.1 |

FOREIGN PATENT DOCUMENTS

| EP | 120694 A | 10/1984 |
| EP | 0239 400 | 9/1987 |
| WO | 8601533 | 3/1986 |

OTHER PUBLICATIONS

Abstracts of oral presentations, Riechman et al, "Recombinant Antibodies," University of London . . . Medical School (1997).
Riechmann, L. et al. "Reshaping human antibodies for . . . "Nature, vol. 332, Mar. 24, 1988, pp. 323–327.
Jones, P.T. et al. "Replacing the complementarity . . . " Nature, vol. 321, May 29, 1986, pp. 522–525.
G. Hale et a. "Effects of monoclonal . . . " Mol. Biol. Med. (1983) 1, pp. 321–334.
S. Roberts et al. "Generation of an antibody . . . "Nature, vol. 328, (1987), pp. 731–734.
G. Hale et al. "Isolation of low–frequency . . . " Jour. of Immunological Methods, 103(1987), pp. 59–67.
Hale et al. "Removable of T cells from bone . . . " Mol. Biol. Med., 1983, 1, pp. 305–319.
Hale et al. "Removal of T cells from . . . " Blood, 1983, 62, pp. 873–882.
Hale et al. "Pilot study of . . . "Transplantation, 1986, 42, pp. 308–311.
Hale et al. "Remission induction . . . " The Lancet, Dec. 17, 1988, pp. 1394–1399.
Schumaker et al. "Ultracentrifuge . . . " Biochemistry, 1976, 15, pp. 5175–5181.
Liu et al. "Chimeric mouse–human . . . "Proc. Natl Acad. of Sci. USA, 1987, 84, pp. 3439–3442.
Shaw et al. "Characterization of a mouse/human . . . " Jour of Immunol., 1987, 138m, pp. 4534–4538.
Bruggemann et al. "Comparison of the effector . . . " J. Exp. Med. 1987, 166, pp. 1351–1361.
Bindon. "Human monoclonal IgG . . . " J. Exp. Med. 1988, 168, pp. 127–142.
Stepleswki et a. "Biological activity of human–. . . " Proc. Natl. Acad. of Sci. USA, 1988, 85, pp. 4852–4856.
Dangl et al. "Segmental flexibility . . . " EMBO Journal, 1988, 7, pp. 1989–1994.
M. Verhoeyen et al. "Reshaping human antibodies . . . " Science, vol. 239, Mar. 25, 1988, pp. 1534–1536.
G. Hale et a. "Therapeutic Potential of Rat Monoclonal Antibodies . . . " The Journal of Immunology, vol. 134 No. 5 (May 1985), pp. 3056–3061.

* cited by examiner

Primary Examiner—James Housel
Assistant Examiner—Stacy S. Brown
(74) Attorney, Agent, or Firm—Nixon & Vanderhye

(57) ABSTRACT

An antibody is produced, which will bind effectively with the antigen Campath-1, and which has at least one complementarity determining region of rat origin, as identified in FIG. 2, which may be combined with a range of different foreign variable domain framework regions as desired, including framework regions of human origin.

18 Claims, 13 Drawing Sheets

HindIII
5'.. ↓  .ATGCAAATCCTCTGAATCTACATGGTAAATATAGGTTTGTCTATACC
■——→ RNA starts    ■——→ RNA starts
ACAAACAGAAAAACATGAGATCACAGTTCTCTCTACAGTTACTGAGCACACAGGACCTCA +60
            signal                              | Splice
         (M  G  W  S  C  I  I  L  F  L  V  A  T  A  T)↓
CCATGGGATGGAGCTGTATCATCCTCTTCTTGGTAGCAACAGCTACAGGTAAGGGGCTCA +120
ATGAAGTTGTGGCTGAACTGGATTTTCCTTTTAACACTTTTAAAT
(M  K  L  W  L  N  W  I  F  L  L  T  L  L  N)

CAGTAGCAGGCTTGAGGTCTGGACATATATATGGGTGACAATGACATCCACTTTGCCTTT +180
   Splice↓        oligos III, IV, VII
         signal    1         5         10
         (G  V  H  S) Q  V  Q  L  Q  E  S  G  P  G  L  V  R
CTCTCCACAGGTGTCCACTCCCAGGTCCAACTGCAGGAGAGCGGTCCAGGTCTTGTGAGA +240
             GGTATCCAGTGTGAGGTGAAACTGTTGGAATCTGGAGGAGGCTTGGTACAG
         (G  I  Q  C) E  V  K  L  L  E  S  G  G  G  L  V  Q
                                       oligo XIII      oligo X
  15             20             25           30*      CDR 1
  P  S  Q  T  L  S  L  T  C  T  V  S  G  S* T  F  S* |D  F  Y|
CCTAGCCAGACCCTGAGCCTGACCTGCACCGTGTCTGGCAGCACCTTCAGCGATTTCTAC +300
CCGGGGGGTTCTATGAGACTCTCCTGTGCAGGTTCTGGATTCACCTTCACTGATTTCTAC
  P  G  G  S  M  R  L  S  C  A  G  S  G  F  T  F  T |D  F  Y|

35     oligo IX    40             45         50    52  a
 |M  N| W  V  R  Q  P  P  G  R  G  L  E  W  I  G |F  I  R  D|
ATGAACTGGGTGAGACAGCCACCTGGACGAGGTCTTGAGTGGATTGGATTTATTAGAGAC +360
ATGAACTGGATCCGCCAGCCTGCAGGGAAGGCACCTGAGTGGCTGGGTTTTATTAGAGAC
 |M  N| W  I  R  Q  P  A  G  K  A  P  E  W  L  G |F  I  R  D|
         oligo XI
  b  c 53     55    CDR 2     60             65           70
      |K  A  K  G  Y  T  T  E  Y  N  P  S  V  K  G| R  V  T  M  L
AAAGCTAAAGGTTACACAACAGAGTACAATCCATCTGTGAAGGGGAGAGTGACAATGCTG +420
AAAGCTAAAGGTTACACAACAGAGTACAATCCATCTGTGAAGGGGCGGTTCACCATCTCC
      |K  A  K  G  Y  T  T  E  Y  N  P  S  V  K  G| R  F  T  I  S 75             80    82 a  b  c 83      85
 V  D  T  S  K  N  Q  F  S  L  R  L  S  S  V  T  A  A  D  T
GTAGACACCAGCAAGAACCAGTTCAGCCTGAGACTCAGCAGCGTGACAGCCGCCGACACC +480
AGAGATAATACCCAAAACATGCTCTATCTTCAAATGAACACCCTAAGAGCTGAGGACACT
 R  D  N  T  Q  N  M  L  Y  L  Q  M  N  T  L  R  A  E  D  T
                                    oligo XII
  90             95    CDR 3    100  a  b 101         105
 A  V  Y  Y  C  A  R |E  G  H  T  A  A  P  F  D  Y| W  G  Q
GCGGTCTATTATTGTGCAAGAGAGGGCCACACTGCTGCTCCTTTTGATTACTGGGGTCAA +540
GCCACTTACTACTGTGCAAGAGAGGGCCACACTGCTGCTCCTTTTGATTACTGGGGCCAA
 A  T  Y  Y  C  A  R |E  G  H  T  A  A  P  F  D  Y| W  G  Q
       oligos V, VI, VII
           110       113    | Splice
 G  S  L  V  T  V  S  S ↓                                  ↓BamHI
GGCAGCCTCGTCACAGTCTCCTCAGGT..........................↙..3' +600
GGAGTCATGGTCACAGTCTCCTCA
 G  V  M  V  T  V  S  S Oligonucleotides: I: 5'-GGC CAG TGG ATA GAC-3', III: 5'-CAG TTT CAT CTA
GAA CTG GAT A-3', IV: 5'-GCA GTT GGG TCT AGA AGT GGA CAC C-3',
V: 5'-TCA GCT GAG TCG ACT GTG AC-3', VI: 5'-TCA CCT GAG TCG ACT GTG
AC-3', VII: 5'-AGT TTC ACC TCG AGG TGG ACA CCT-3', VIII: 5'-TCA CCT GAG
GAG ACT GTG AC-3'; IX: 5'-GGC TGG CGA ATC CAG TT-3', X: 5'-CTG TCT CAC
CCA GTT CAT GTA GAA ATC GCT GAA GGT GCT-3', XI: 5'-CAT TGT CAC TCT
CCC CTT CAC AGA TGG ATT GTA CTC TGT TGT GTA ACC TTT AGC TTT GTC
TCT AAT AAA TCC AAT CCA CTC-3', XII. 5'-GCC TTG ACC CCA GTA ATC AAA
AGG AGC AGC AGT GTG GCC CTC TCT TGC ACA ATA-3', XIII 5'-AGA AAT
CGG/C TGA AGG TGA AGC CAG ACA C-3'

Fig. 2a

```
Hind III
5'....↓......ATGCAAATCCTCTGAATCTACATGGTAAATATAGGTTTGTCTATACC
  ■——→RNA starts      ■——→RNA starts
ACAAACAGAAAAACATGAGATCACAGTTCTCTCTACAGTTACTGAGCACACAGGACCTCA  +60
                                                        ATGA
                                                         Ⓜ
      signal                              Splice
   ⟨M  G  W  S  C  I  I  L  F  L  V  A  T  A  T⟩ ↓
CCATGGGATGGAGCTGTATCATCCTCTTCTTGGTAGCAACAGCTACAGGTAAGGGGCTCA  +120
TGGCTGCACTTCAACTCTTAGGGGTAGCTGCTAGCTCTGGCTCCCAG
 ⟨M  A  A  L  Q  L  L  G  V  A  A  S  S  G  S  Q⟩

CAGTAGCAGGCTTGAGGTCTGGACATATATATGGGTGACAATGACATCCACTTTGCCTTT  +180
    Splice↓signal    1           5              10
         ⟨G  V  H  S⟩ D  I  Q  M  T  Q  S  P  S  S  L  S  A
CTCTCCACAGGTGTCCACTCCGACATCCAGATGACCCAGAGCCCAAGCAGCCTGAGCGCC  +240
              GCCATGAGATGTGACATCAAGATGACCCAGTCTCCCTCATTCCTGTCTGCA
         ⟨A  M  R  C⟩ D  I  K  M  T  Q  S  P  S  F  L  S  A
                                    oligo XIV
   15             20            25            30    CDR 1
    S  V  G  D  R  V  T  I  T  C  ⌈K  A  S  Q  N  I  D  K  Y  L⌉
AGCGTGGGTGACAGAGTGACCATCACCTGTAAAGCAAGTCAGAATATTGACAAATACTTA  +300
TCTGTGGGAGACAGAGTCACTCTCAACTGCAAAGCAAGTCAGAATATTGACAAATACTTA
    S  V  G  D  R  V  T  L  N  C  ⌈K  A  S  Q  N  I  D  K  Y  L⌉
                                         oligo XV
   35            40            45            50   CDR 2
⌈N⌉ W  Y  Q  Q  K  P  G  K  A  P  K  L  L  I  Y  ⌈N  T  N  N⌉
AACTGGTACCAGCAGAAGCCAGGTAAGGCTCCAAAGCTGCTGATCTACAATACAAACAAT  +360
AACTGGTATCAGCAAAAGCTTGGAGAATCTCCCAAACTCCTGATATATAATACAAACAAT
⌈N⌉ W  Y  Q  Q  K  L  G  E  S  P  K  L  L  I  Y  ⌈N  T  N  N⌉

55            60            65            70
⌈L  Q  T⌉ G  V  P  S  R  F  S  G  S  G  S  G  T  D  F  T  F
TTGCAAACGGGTGTGCCAAGCAGATTCAGCGGTAGCGGTAGCGGTACCGACTTCACCTTC  +420
TTGCAAACGGGCATCCCATCAAGGTTCAGTGGCAGTGGATCTGGTACTGATTTCACACTC
⌈L  Q  T⌉ G  I  P  S  R  F  S  G  S  G  S  G  T  D  F  T  L
                                           oligo XVI
   75            80            85            90   CDR 3
    T  I  S  S  L  Q  P  E  D  I  A  T  Y  Y  C  ⌈L  Q  H  I  S⌉
ACCATCAGCAGCCTCCAGCCAGAGGACATCGCCACCTACTACTGCTTGCAGCATATAAGT  +480
ACCATCAGCAGCCTGCAGCCTGAAGATGTTGCCACATATTTCTGCTTGCAGCATATAAGT
    T  I  S  S  L  Q  P  E  D  V  A  T  Y  F  C  ⌈L  Q  H  I  S⌉

95          100          105      108
⌈R  P  R  T⌉ F  G  Q  G  T  K  V  E  I  K  R
AGGCCGCGCACGTTCGGCCAAGGGACCAAGGTGGAAATCAAACGTGAGTAGAATTTAAAC  +540
AGGCCGCGCACGTTTGGAACTGGGACCAAGCTGGAGCTGAAACGG
⌈R  P  R  T⌉ F  G  T  G  T  K  L  E  L  K  R
            BamHI
TTTGCTTCCTCAGTTGGATCC-3'

Oligonucleotides: II: 5'-TGC AGC ATC AGC C-3', XIV: 5'-CTG CTG GTA CCA
GTT TAA GTA TTT GTC AAT ATT CTG ACT TGC TTT ACA GGT GAT GGT-3',
XV: 5'-GCT TGG CAC ACC CGT TTG CAA ATT GTT TGT ATT GTA GAT CAG
CAG-3', XVI: 5'-CCC TTG GCC GAA CGT GCG CGG CCT ACT TAT ATG CTG CAA
GCA GTA GTA GGT-3'.
```

Fig. 2b

Sequence of the synthetic gene HUVLLYSO

```
          D   I   Q   M   T   Q   S   P   S   S   L   S   A   S   V   G   D   R   V
CTGCA GACATCCAGATGACCCAGAGCCCAAGCAGCCTGAGCGCCAGCGTGGGTGACAGAG
GACGT CTGTAGGTCTACTGGGTCTCGGGTTCGTCGGACTCGCGGTCGCACCCACTGTCTC
         10        20        30        40        50        60

T   I   T   C   R   A   S   G   N   I   H   N   Y   L   A   W   Y   Q   Q   K
TGACCATCACCTGTAGAGCCAGCGGTAACATCCACAACTACCTGGCTTGGTACCAGCAGA
ACTGGTAGTGGACATCTCGGTCGCCATTGTAGGTGTTGATGGACCGAACCATGGTCGTCT
         70        80        90       100       110       120

P   G   K   A   P   K   L   L   I   Y   Y   T   T   T   L   A   D   G   V   P
AGCCAGGTAAGGCTCCAAAGCTGCTGATCTACTACACCACCACCCTGGCTGACGGTGTGC
TCGGTCCATTCCGAGGTTTCGACGACTAGATGATGTGGTGGTGGGACCGACTGCCACACG
        130       140       150       160       170       180

S   R   F   S   G   S   G   S   G   T   D   F   T   F   T   I   S   S   L   Q
CAAGCAGATTCAGCGGTAGCGGTAGCGGTACCGACTTCACCTTCACCATCAGCAGCCTCC
GTTCGTCTAAGTCGCCATCGCCATCGCCATGGCTGAAGTGGAAGTGGTAGTCGTCGGAGG
        190       200       210       220       230       240

P   E   D   I   A   T   Y   Y   C   Q   H   F   W   S   T   P   R   T   F   G
AGCCAGAGGACATCGCCACCTACTACTGCCAGCACTTCTGGAGCACCCCAAGGACGTTCG
TCGGTCTCCTGTAGCGGTGGATGATGACGGTCGTGAAGACCTCGTGGGGTTCCTGCAAGC
        250       260       270       280       290       300

Q   G   T   K   V   E   I   K   R
GCCAAGGGACCAAGGTGGAAATCAAACGTGAGTAGAATTTAAACTTTGCTTCCTCAGTTG
CGGTTCCCTGGTTCCACCTTTAGTTTGCACTCATCTTAAATTTGAAACGAAGGAGTCAAC
        310       320       330       340       350       360

GATCCTAGAATTC
CTAGGATCTTAAG
        370
```

Fig. 3

```
                                                   ATGCAAATCCTCTGAAT
CTACATGGTAAATATAGGTTTGTCTATACCACAAACAGAAAAACATGAGATCACAGTTCT

M  G  W  S  C  I  I  L  F
CTCTACAGTTACTGAGCACACAGGACCTCACCATGGGATGGAGCTGTATCATCCTCTTCT

L  V  A  T  A  T
TGGTAGCAACAGCTACAGGTAAGGGGCTCACAGTAGCAGGCTTGAGGTCTGGACATATAT

1
                                              G  V  H  S  D  I  Q
ATGGGTGACAATGACATCCACTTTGCCTTTCTCTCCACAGGTGTCCACTCCGACATCCAG 5              10             15             20
 M  T  Q  S  P  S  S  L  S  A  S  V  G  D  R  V  T  I  T  C
ATGACCCAGAGCCCAAGCAGCCTGAGCGCCAGCGTGGGTGACAGAGTGACCATCACCTGT

******************************
        25             30             35             40
 R  A  S  G  N  I  H  N  Y  L  A  W  Y  Q  Q  K  P  G  K  A
AGAGCCAGCGGTAACATCCACAACTACCTGGCTTGGTACCAGCAGAAGCCAGGTAAGGCT

*******************
        45             50             55             60
 P  K  L  L  I  Y  Y  T  T  T  L  A  D  G  V  P  S  R  F  S
CCAAAGCTGCTGATCTACTACACCACCACCCTGGCTGACGGTGTGCCAAGCAGATTCAGC 65             70             75             80
 G  S  G  S  G  T  D  F  T  F  T  I  S  S  L  Q  P  E  D  I
GGTAGCGGTAGCGGTACCGACTTCACCTTCACCATCAGCAGCCTCCAGCCAGAGGACATC

*********************
        85             90             95             100
 A  T  Y  Y  C  Q  H  F  W  S  T  P  R  T  F  G  Q  G  T  K
GCCACCTACTACTGCCAGCACTTCTGGAGCACCCCAAGGACGTTCGGCCAAGGGACCAAG 105      108
 V  E  I  K  R
GTGGAAATCAAACGTGAGTAGAATTTAAACTTTGCTTCCTCAGTTGGATCCTAGAATTC
```

Fig.4

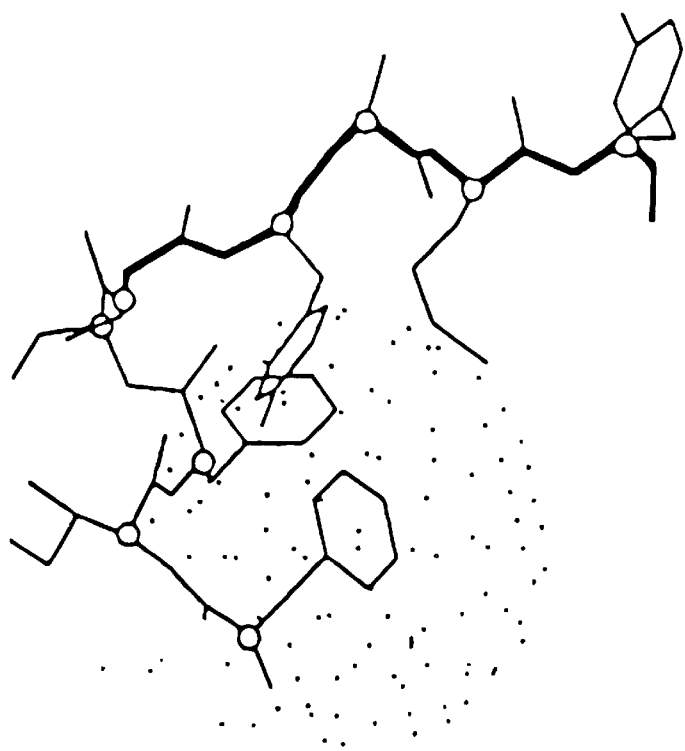
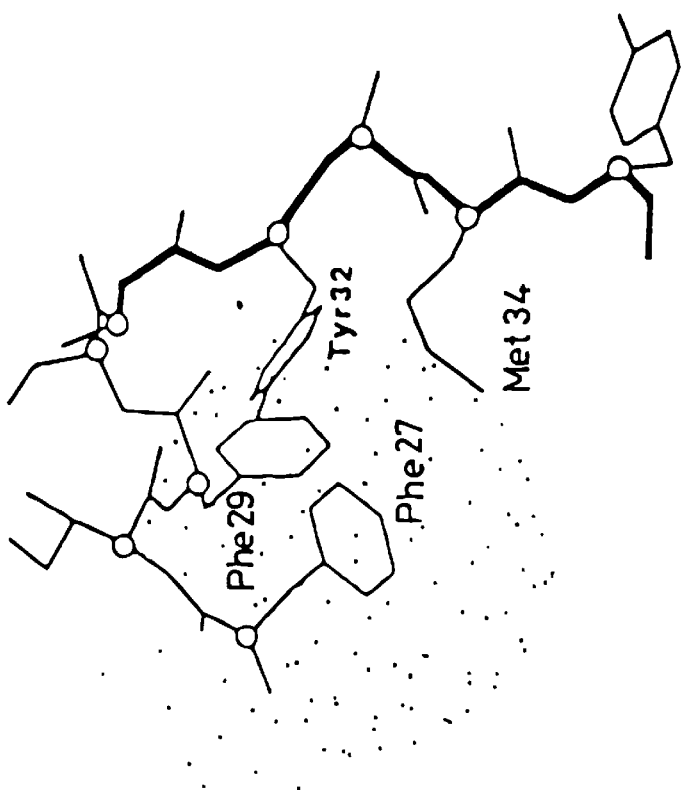
Fig. 6

Fig.10a
Fig.10b
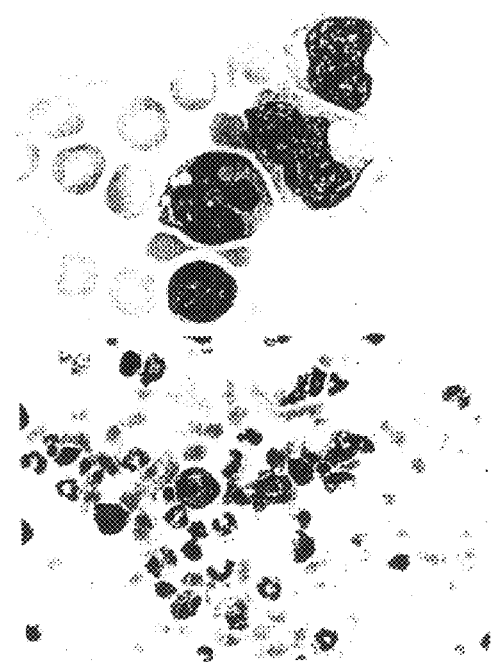
Fig.10c
Fig.10d

ANTIBODIES TO THE ANTIGEN CAMPATH-1

This is a Rule 60 divisional of application Ser. No. 08/235,705, filed Apr. 29, 1994, now U.S. Pat. No. 5,846,534 which is a continuation of application Ser. No. 08/099,480, filed Jul. 30, 1993, now abandoned, which is a continuation of application Ser. No. 07/921,601, filed Aug. 3, 1992, now abandoned, which is a continuation of application Ser. No. 07/424,233, filed Oct. 12, 1989, now abandoned.

FIELD OF THE INVENTION

This invention relates to antibodies.

BACKGROUND TO THE INVENTION

Antibodies, or immunoglobulins, comprise two heavy chains linked together by disulphide bonds and two light chains, each light chain being linked to a respective heavy chain by disulphide bonds. The general structure of an antibody of class IgG (i.e. an immunoglobulin (Ig) of class gamma (G)) is shown schematically in FIG. 1 of the accompanying drawings.

Each heavy chain has at one end a variable domain followed by a number of constant domains. Each light chain has a variable domain at one end and a constant domain at its other end, the light chain variable domain being aligned with the variable domain of the heavy chain and the light chain constant domain being aligned with the first constant domain of the heavy chain. The constant domains in the light and heavy chains are not involved directly in binding the antibody to antigen.

The variable domains of each pair of light and heavy chains form the antigen binding site. The domains on the light and heavy chains have the same general structure and each domain comprises four framework regions, whose sequences are relatively conserved, connected by three complementarity determining regions (CDRs) (see reference 11). The four framework regions largely adopt a beta-sheet conformation and the CDRs form loops connecting, and in some cases forming part of, the beta-sheet structure.

The CDRs are held in close proximity by the framework regions and, with the CDRs from the other domain, contribute to the formation of the antigen binding site.

SUMMARY OF THE INVENTION

According to one aspect of the present invention there is provided an antibody having at least one CDR which is foreign with respect to the constant region of the antibody, said at least one foreign CDR being selected from CDRs substantially as identified in FIG. 2, namely residues 31 to 35 (SEQ ID NO:1), 50 to 65 (SEQ ID NO:2) and 95 to 102 (SEQ ID NO:3), of the heavy chain and residues 24 to 34, 50 to 56 and 89 to 97 of the light chain, the antibody being capable of binding effectively to the antigen Campath-1.

The term "foreign" is used in relation to the CDR(s) and constant region to mean of different origin.

In FIG. 2 and elsewhere in the specification amino acid residues are identified by the conventionally used one letter symbols, as follows:

| Amino Acid | One-letter symbol |
| --- | --- |
| Alanine | A |
| Arginine | R |
| Asparagine | N |
| Aspartic acid | D |
| Asparagine or aspartic acid | B |
| Cysteine | C |
| Glutamine | Q |
| Glutamic acid | E |
| Glutamine or glutamic acid | Z |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

In this specification, effective antibody-antigen binding is used to mean that antibody effects 50% binding to antigen at antibody concentrations of less than or equal to 70 ug/ml, preferably at concentrations of less than or equal to 7 ug/ml. Binding affinity may be tested by assay procedures such as are described in Example 1 herein, eg using Campath-1 antigen obtained from a glycolipid extract from human spleen. (ug=microgram)

Thus, a standard procedure for the extraction of glycolipids can be applied to the extraction of the Campath-1 antigen from human spleens. This standard extraction procedure involves the treatment of 1 volume of homogenised human spleen tissue with 3 volumes of water, 11 volumes of methanol and 5.4 volumes of chloroform. After mixing precipitated material is discarded and a further 3.5 volumes of water are added, followed by further mixing. The mixture is then allowed to separate into two phases, the lower chloroform-containing phase is discarded and the upper aqueous phase is concentrated to provide a crude extract of the Campath-1 antigen, which can if desired be purified further by affinity chromatography, for example using the YTH66.9 antibody referred to hereinafter.

The antibody of the present invention desirably has a light chain with at least one CDR selected from CDRs substantially as identified in FIG. 2 and a heavy chain with at least one CDR selected from CDRs substantially as identified in FIG. 2.

As a further possibility, the antibody of the present invention preferably has three heavy chain CDRs substantially as identified in FIG. 2, or three light chain CDRs substantially as identified in FIG. 2. More preferably, the antibody has all six heavy and light chain CDRs substantially as identified in FIG. 2.

Hence, in a preferred aspect the present invention provides an antibody having heavy and light chain CDRs which are foreign with respect to the constant region of the antibody, said CDRs being substantially as identified in FIG. 2, namely residues 31 to 35, 50 to 65 and 95 to 102 of the heavy chain and residues 24 to 34, 50 to 56 and 89 to 97 of the light chain, the antibody being capable of binding effectively to the antigen Campath-1.

The CDRs identified in FIG. 2 are of rat origin and may be combined with a range of different variable domain framework regions, as desired, including, eg, framework regions of rat or human origin.

In a further aspect the present invention provides an antibody having heavy and light chain variable domains as identified in the lower lines of sequence information in FIG. 2, namely residues 1 to 113 (SEQ ID NO:7) of the heavy chain and residues 1 to 108 (SEQ ID NO:8) of the light chain, the CDRs and constant region of the antibody being foreign with respect to one another, the antibody being capable of binding effectively to the antigen Campath-1.

Such an antibody comprises CDRs and framework regions of rat origin.

The invention also provides an antibody having heavy and light chain variable domains as identified in the upper lines of sequence information in FIG. 2, namely residues 1 to 113 (SEQ ID NO:9) of the heavy chain and residues 1 to 108 (SEQ ID NO:10) of the light chain, and that will bind effectively to the antigen Campath-1.

Such an antibody comprises CDRs of rat origin in framework regions of human origin.

Such an antibody may be modified by having a phenylalanine group at residue 27 of the heavy chain in place of serine, and possibly also by having a threonine group at residue 30 of the heavy chain in place of serine. A Ser(27) to Phe mutation is found to increase antibody-antigen binding significantly. However, the mutation of Ser (30) to Thr (in the human framework with the Ser (27) to Phe mutation) has little effect on binding affinity. This illustrates that point mutations in the antibody may have a major effect or little effect on the affinity of the antibody for the antigen. Although the two changes Ser (27) to Phe and Ser (30) to Thr are located within the framework region as defined in reference 11, they lie within the hypervariable loop Hl as defined in reference 18. It is accordingly believed that some changes in the CDRs may similarly be made without necessarily having an adverse effect on antibody-antigen affinity. References to CDRs substantially as identified in FIG. 2 are accordingly intended to include within their scope not only CDRs identical to those identified in FIG. 2 but also variants of such CDRs, subject to the requirement of the antibody binding effectively to Campath-1.

The antibody is preferably in biologically pure form, desirably being at least 95% (by wt) free of other biological materials.

The remainder of the antibody, namely the heavy and light chain constant domains and possibly also variable domain framework regions and one or more CDRs, can be based on antibodies of various different types as desired including, eg, rat and human antibodies of different classes. Thus, the constant domains can be selected to have desired effector functions appropriate to the intended use of the antibody. For example, for therapeutic purposes, human IgG1 and rat IgG2b are currently favoured isotypes. Further, of the human IgG isotypes, IgG1 and IgG3 appear to be the most effective for complement and cell mediated lysis, and therefore for killing tumour cells. For other purposes other isotypes may be favoured, eg, rat IgM, IgG1, IgG2a, IgG2c, human IgG2, IgG4 etc. For human therapy it is particularly desirable to use human isotypes, to minimise antiglobulin responses during therapy.

The Campath-1 antigen is strongly expressed on virtually all human lymphocytes and monocytes, but is absent from other blood cells including the hemopoietic stem cells, the antigen being described by Hale et al in Blood, 1983, 62, 873–882 (reference 6). That paper describes the antibody YTH66.9 which is specific for the Campath-1 antigen, this antibody being available from Serotec of 22 Bankside, Station Approach,. Kidlington, Oxford, England, under the designation YTH 66.9 HL. A further series of antibodies to Campath-1 have been produced, including rat monoclonal antibodies of IgM, IgG2a, and IgG2c isotypes (reference 7) and more recently IgG1 and IgG2b isotypes have been isolated as class switch variants from the IgG2a secreting cell line YTH 34.5HL (reference 8). All of these antibodies with the exception of the rat IgG2c isotype are able to efficiently lyse human lymphocytes with human complement.

In addition, the IgG2b antibody YTH 34.5HL-G2b, but not the other isotypes, is effective in antibody dependent cell mediated cytotoxicity (ADCC) with human effector cells (reference 8). These rat monoclonal antibodies have found important application in the context of immunosuppression, for control of graft-versus-host disease in bone marrow transplantation (reference 6); the management of organ rejection (reference 9); the prevention of marrow rejection and in the treatment of various lymphoid malignancies (reference 10). For in-vivo use, the IgG2b antibody YTH 34.5HL-G2b seems to be the most effective at depleting lymphocytes, but the use of any of the antibodies in this group is limited by the antiglobulin response which can occur within two weeks of the initiation of treatment (reference 10).

Antibodies in accordance with the invention, particularly those based on human isotypes, thus have good therapeutic potential. In particular, the availability of a reshaped human antibody with specificity for the Campath-1 antigen should permit a full analysis of the in vivo potency and immunogenicity of an anti-lymphocyte antibody with wide therapeutic potential. Such reshaped antibodies have been used in the treatment of patients with non-Hodgkin lymphoma, as well as in the treatment of some cases of autoimmune disease. Further trials with organ graft patients, particularly kidney graft patients, are proposed. Even if anti-idiotypic responses are eventually observed, considerable therapeutic benefit could be derived by an extended course of treatment. In addition an antiglobulin response restricted to idiotype should be circumvented by using a series of antibodies with different idiotype (reference 20). In principle, the idiotype of the reshaped Campath-1 could be changed by altering the hypervariable regions or the framework regions: evidence from a reshaped antibody specific for the hapten nitrophenyl acetate suggests that the recognition by anti-idiotypic antisera and anti-idiotypic monoclonal antibodies is influenced by residues in the framework region (reference 5). Thus recycling the hypervariable regions on different human framework regions should change the idiotype, although ultimately it could focus the response directly onto the binding site for Campath-1 antigen. Although such focussing would be undesirable for Campath-1 antibodies, it could be an advantage for the development of anti-idiotypic vaccines.

In a further aspect, the invention thus provides a method of treating patients, particularly humans, with cancers, particularly lymphomas, or for immunosuppression purposes, comprising administering antibodies in accordance with the invention.

Antibodies in accordance with the present invention may be formulated for administration to patients by mixing antibody purified in conventional manner with a physiologically acceptable diluent or carrier, possibly in admixture with other therapeutic agents such as other antibodies. In one example, purified antibody was reconstituted in a commercially available human plasma protein solution (minus gamma globulin). The formulation was administered by intravenous infusion at the rate of 5 mg antibody per day for at least 10 days.

Antibodies in accordance with the invention can be produced in various different ways, as will be described in greater detail in the Examples following.

Heavy and light chain variable domains are conveniently produced separately and assembled with the remainder of an antibody of desired origin, eg desired human isotype.

Genes encoding the variable domains of an antibody of desired structure may be produced, and attached to genes encoding the constant domains of an antibody of desired isotype. Genes encoding variable domains can be derived from hybridoma cDNA or from the chromosome. Genes encoding the variable domains are also conveniently constructed by gene synthesis techniques or by site directed mutagenesis using long synthetic oligonucleotides. Expression is conveniently effected by transforming a cell line, eg an immortalised mammalian cell line such as a myeloma cell line, with expression vectors including DNA coding for the variable domains and for the remainder of the antibody and culturing the transfomed cell line to produce the desired antibody.

In another aspect the invention provides a process for the preparation of an antibody having at least one CDR (complementarity determining region) which is foreign with respect of the constant region of the antibody, said at least one foreign CDR being selected from CDRs substantially as identified in FIG. 2, that is amino acid residues 31 to 35, 50 to 65 and 95 to 102 of the heavy chain as shown in FIG. 2a, and amino acid residues 24 to 34, 50 to 56 and 89 to 97 of the light chain as shown in FIG. 2b, the antibody being capable of binding effectively to the antigen Campath-1, which process comprises culturing a cell capable of expressing the antibody in order to effect express-ion thereof.

It will be appreciated that the antibody may be used in a form which retains the CDRs but lacks other parts of the whole molecule not essential to its binding efficacy, in particular a F(ab')$_2$ fragment, and the word antibody is used herein to include such materials.

BRIEF DESCRIPTION OF THE DRAWINGS

The invention will be further described, by way of illustration, in the following Examples which refer to the accompanying drawings, in which:

FIGS. 2a and 2b illustrate nucleic acid and amino acid sequences of the variable domains of antibodies in accordance with the invention, with FIG. 2a representing the heavy chain and FIG. 2b representng the light chain. The upper line of the Figure gives sequence information for reshaped antibody, with the lower line giving sequence information for rat YTH 34.5HL antibody;

FIG. 3 illustrates the sequence of the HuVLLYS° gene and derived amino acid sequence;

FIG. 4 illustrates the sequence of the HuVLLYS gene and derived amino acid sequence;

FIG. 6 illustrate loop Phe 27 to Tyr 35 in the heavy chain variable domain of the human myeloma protein KOL;

FIGS. 10A–D show the cytology of bone marrow cells from two (patients 1 and 2) patients treated with CAMPATH-1H:

Figure 1:
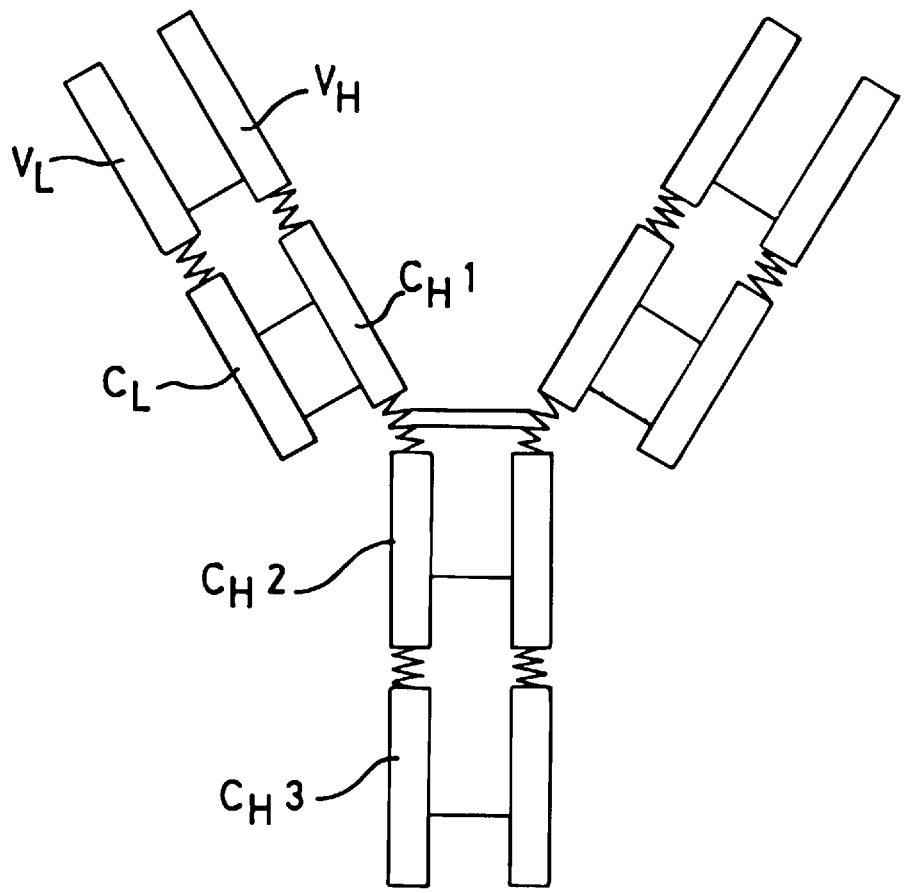
FIG. 1 is a schematic diagram illustrating the structure of an IgG molecule.

A=patient 1 trephine before treatment with CAMPATH-1H

B=patient 1 trephine on day 43 (ie 16 days after treatment)

C=patient 2 aspirate before treatment with CAMPATH-1H

D=patient 2 aspirate on day 78 (ie 35 days after treatment);

FIGS. 11A–D show computed tomography scans from patients 1 and 2, showing affected spleens and lymphonode:

A=patient 1 before treatment with CAMPATH-1H

B=patient 1 on day 57

C=patient 2 before,treatment with CAMPATH-1H (retrocrural node arrowed)

D=patient 2 on day 51; and

Figure 12:
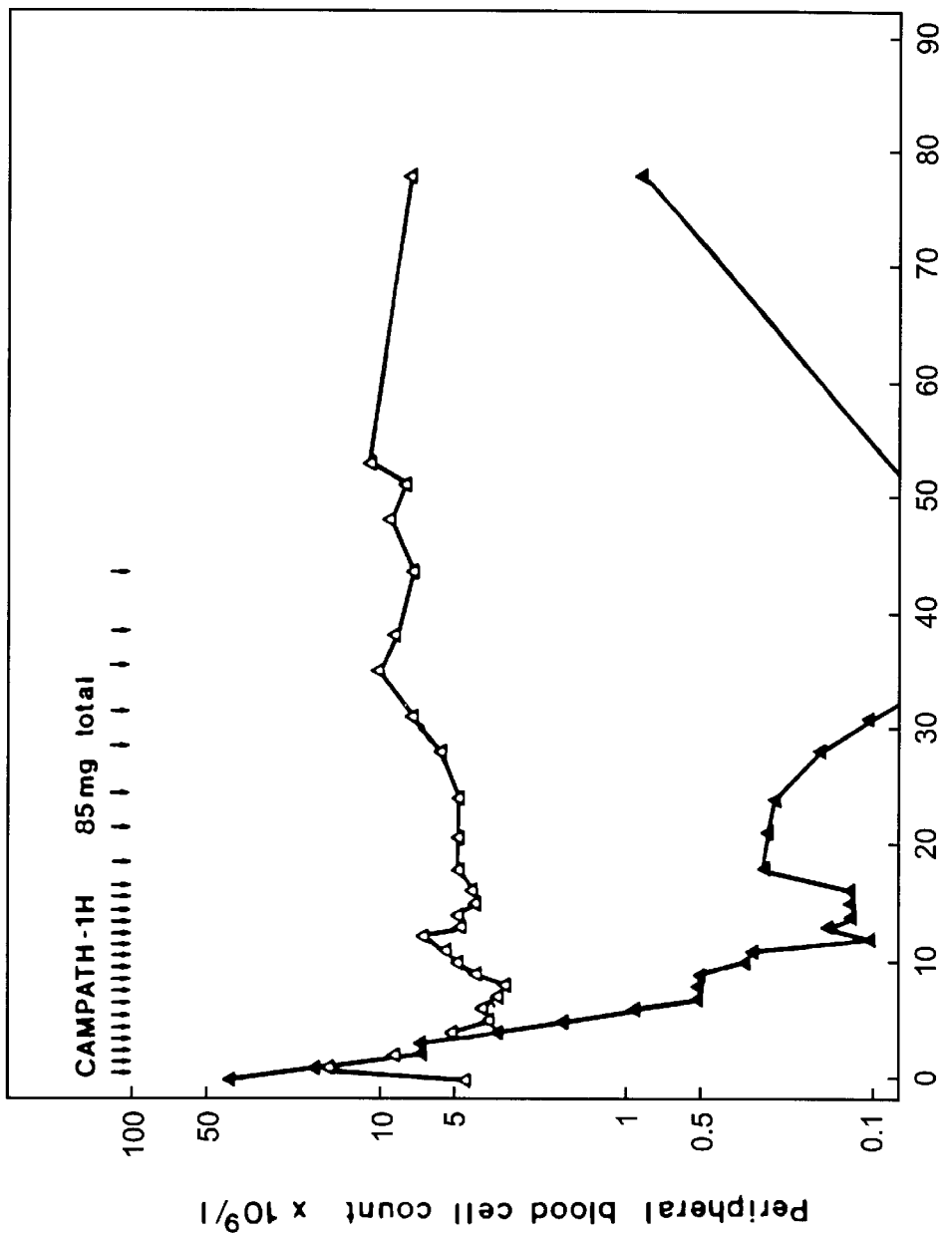

FIG. 12 shows the effect of CAMPATH-1H on blood counts in patient 2, with solid triangles showing results for lymphocytes and empty triangles results for neutrophils.

EXAMPLE 1

The sequences of the heavy and light chain variable domains of rat IgG2a Campath-1 antibody YTH 34.5HL were determined by cloning the cDNA (FIG. 2), and the hypervariable regions were identified according to Kabat (see reference 11). Sequence information is given in the lower lines of FIG. 2, with the CDRs identified in boxes. The heavy chain cDNA sequence is SEQ ID NO:11. The light chain eDNA sequence is SEQ ID NO:12. The protein sequences are SEQ ID NOS:8 and 7 for the light and heavy chains respectively.

In the heavy chain variable domain there is an unusual feature in the framework region. In most known heavy chain sequences Pro(41) and Leu(45) are highly conserved: Pro (41) helps turn a loop distant from the antigen binding site and Leu(45) is in the beta bulge which forms part of the conserved packing between heavy and light chain variable domains (reference 12). In YTH 34.5HL these residues are replaced by Ala(41) and Pro(45), and presumably this could have some effect on the packing of the heavy and light chain variable domains.

Working at the level of the gene and using three large mutagenic oligonucleotides for each variable domain, in a single step the hypervariable regions of YTH 34.5HL were mounted on human heavy or light chain framework regions taken from the crystallographically solved proteins NEW for the heavy chain (reference 13) and from a protein based closely on the human myeloma protein REI for the light chain (reference 14). The NEW light chain was not used because there is a deletion at the beginning of the third framework region of the NEW light chain. The resulting reshaped heavy chain variable domain HuVHCAMP is based on the HuVHNP gene (references 1, 5) with the framework regions of human NEW alternating with the hypervariable regions of rat YTH 34.5HL. There are discrepancies involving the first framework region and the first hypervariable loop of the NEW heavy chain between the published sequence used here and the sequence deposited in the Brookhaven data base (in parentheses): Ser27 (to Thr), Thr28 (to Ser) and Ser30 (to Asp). Neither version is definitive and the discrepancies do not affect present considerations. The reshaped light chain variable domain HuVLCAMP is a similar construct, except with essentially the framework regions of the human myeloma protein REI, with the C-terminal and the 3' non-coding sequence taken from a human $J_k$-region sequence (reference 22). Sequence information for the variable domain of the reshaped antibody is given in the upper lines in FIG. 2. SEQ ID NOS:13 and 14 show the cDNA sequences for the heavy and light chains respectively. The sequences of oligonucleotide primers are given and their locations on the genes are also marked in FIG. 2. These primers have been designated SEQ ID NOS:15 to 30.

Considering the above in further detail, mRNA was purified (reference 23) from the hybridoma clone YTH 34.5HL (gamma 2a, $k^b$), and first strand cDNA made by priming with oligonucleotides complementary to the 5' end of the CH1 (oligonucleotide I) and the Ck exons (oligonucleotide II). cDNA was cloned and sequenced as described in references 24 and 25.

For expression of the rat heavy chain variable domain RaVHCAMP, two restriction sites (XbaI and SalI) were introduced at each end of the cDNA clone in M13 using mutagenic oligonucleotides III and V respectively, and the XbaI-SalI fragment excised. Simultaneously, the corresponding sites were introduced into the M13-HuVHNP gene using oligonucleotides IV and VI, and the region between the sites exchanged. The sequence at the junctions was corrected with oligonucleotides VII and VIII, and an internal BamHI site removed using the oligonucleotide IX, to create the M13-RaVHCAMP gene. The encoded sequence of the mature domain is thus identical to that of YTH 34.5HL.

The reshaped heavy chain variable domain (HuVHCAMP) was constructed in an M13 vector by priming with three long oligonucleotides simultaneously on the single strand containing the M13-HuVHNP gene.(references 1, 5). The mutagenesis techniques used were similar to those described in reference 33, using the host 71-18 mutL and without imposing strand selection. Each oligonucleotide (X, XI and XII) was designed to replace each of the hypervariable regions with the corresponding region from the heavy chain of the YTH 34.5HL antibody.

Colony blots were probed initially with the oligonucleotide X and hybridisation positives were sequenced: the overall yield of the triple mutant was 5%. Ser27 to Phe and Ser27 to Phe, Ser30 to Thr mutants (to be described below) of M13mp8-HuVHCAMP were made with the mixed oligonucleotide XIII.

The reshaped light chain variable domain (HuVLCAMP) was constructed in an M13 vector from a gene with framework regions based on human REI. As above, three long oligonucleotides (XIV, XV, and XVI) were used to introduce the hypervariable regions of the YTH 34.5HL light chain.

Construction of the humanised light chain variable domain is described in greater detail in the following seven paragraphs.

(1) The "humanised" light chain variable domain (HuVLCAMP) was constructed in three stages, utilising a "humanised" light chain variable domain (HUVLLYS) which had been constructed for other purposes.

(a) The first stage involved the gene synthesis of a "humanised" light chain variable domain gene (HuVLLYS°). The HuVLLYS° gene incorporates human framework regions identical to the most common residue in each position in the Kabat alignment of the human kappa subgroup I, except for residues 97–108, which were identical to those in the human J1 fragment described in reference 34. The sequences of the framework regions are very similar to the crystallographically solved light chain structure REI. The CDRs in HuVLLY°s were identical to those in the mouse antilysozyme antibody (D1.3) light chain (unpublished). A 30 bp sequence, identical to the sequence following the genomic JI segment, was introduced to the 3' side of residue 108. BamHl and EcoRI restriction sites were introduced at the 3' end of the synthetic gene, and a PstI site at the 5' end. The gene synthesis of HuVLLYS° is described in paragraphs (2) to (5) below, and the sequence of the gene and the derived amino acid sequence is given in FIG. 3. These are identified as SEQ ID NOS:31 and 32 respectively.

(b) The second stage involved the introduction of the HuVLLYS° gene in place of the heavy chain variable domain in the vector M13-MOVHNP and this is described in pargraphs 6 and 7 below. Thus the light chain variable domain utilises the promoter and signal sequence of a heavy chain variable domain: at the 3' end of the gene the sequence is derived from the human light chain J1 segment as described in paragraph (1a). The sequence of the HuVLLYS gene and the derived amino acid sequence is given in FIG. 4. These sequences are identified as SEQ ID NO:33 and 34 respectively.

(c) The third stage involved the conversion of HuVLLYS to a "humanised" light chain variable domain with the CDRs of Campath-1 specificity.

2. For the synthesis of the HuVLLYS° gene, three blocks of oligonucleotides (PK1-5, KK1-5 and KE1-8 in the table in paragraph 3 below were cloned separately into M13 vectors, and sequenced. Each cloned block was excised and ligated together into M13mp19 to create the HuVLLYS° gene.

3. Oligonucleotides listed below were produced on an Applied Biosystems 380B synthesizer. Each oligonucleotide was size-purified, 10 nmol being subjected to electrophoresis on a 20×40 cm 12% polyacrylamide, 7M urea gel, eluted from the gel by dialysis against water, and lyophilized. For gene synthesis or mutagenesis, a 50 pmol aliquot of each purified oligonucleotide was phosphorylated in a 20 ul reaction mixture with 50 mM Tris-Cl (pH 8.0), 10 mM $MgCl_2$, 5 mM dithiothreitol, 1 mM ATP, and 5 units of polynucleotide kinase, incubated at 37° for 30 minutes. When used as hybridization probes, gel-purified oligonucleotides were phosphorylated in a similar fashion, except on a 15 pmol scale with an excess of $^{32}P$ labeled ATP.

| name | sequence (5'-3') (SEQ ID NOS:35 to 53) |
|---|---|
| PK1 | GACATCCAGATGACCCAGAGCCCAAGCAGCCTGAGCGCCAGCGTGGGT |
| PK2 | GACAGAGTGACCATCACCTGTAGAGCCAGCGGTAACATCCACAACTAC CTGGCTTGGTAC |
| PK3 | CAAGCCAGGTAGTTGTGGATGTTACCGCTGGCTCTACAGGTGAT |
| PK4 | GGTCACTCTGTCACCCACGCTGGCGCTCAGGCT |
| PK5 | GCTTGGGCTCTGGGTCATCTGGATGTCTGCA |
| KK1 | CAGCAGAAGCCAGGTAAGGCTCCAAAGCTGCTGATCTACTACACCACC A |
| KK2 | CCCTGGCTGACGGTGTGCCAAGCAGATTCAGCGGTAGCGGTAGCGGTA C |
| KK3 | CGCTACCGCTACCGCTGAATCTGCT |
| KK4 | TGGCACACCGTCAGCCAGGGTGGTGGTGTAGTAGATCAGC |
| KK5 | AGCTTTGGAGCCTTACCTGGCTTCTGCTGGTAC |
| KE1 | CGACTTCACCTTCACCATCAGCAGCCTCCAGCCAGAGGACATCGCCAC CTACTACTGCC |
| KE2 | AGCACTTCTGGAGCACCCCAAGGACGTTCGGCCAAGGGACCAAGGTGG A |
| KE3 | AATCAAACGTGAGTAGAATTTAAACTTTGCTTCCTCAGTTGGATCCTA G |
| KE4 | AATTCTAGGATCCAACTGAGGAAGCAAAGTTTAAA |
| KE5 | TTCTACTCACGTTTGATTTCCACCTTGGTCCCTT |
| KE6 | GGCCGAACGTCCTTGGGGTGCTCCAGAAGTGCTGGCAGTAGTAG |
| KE7 | GTGGCGATGTCCTCTGGCTGGAGGCT |
| KE8 | GCTGATGGTGAAGGTGAAGTCGGTAC |
| PK0 | TCATCTGGATGTCGGAGTGGACACCT |

4. The construction of individual blocks is described for the PK1-5 block, but KK1-5 and KE1-8 blocks were cloned as KpnI-KpnI and KpnI-EcoRI fragments respectively in a similar way. 4 ul portions of each oligonucleotide PK1, PK2, PK3, PK4 and PK5, kinased as in paragraph 3, were combined and annealed at 80° C. for 5 minutes, 67° C. for 30 minutes, and allowed to cool to room temperature over the span of 30 minutes, 0.1 ul of this annealing mix was ligated with 20 ng of PstI/KpnI digested M13-mp19, in 10 ul 50 mM Tris-Cl (pH7.5), 10 mM MgCl$_2$, 10 mM dithiothreitol, 1 mM ATP, 120 units T4 DNA ligase (Biolabs), and incubated 12 hours at 15° C. The ligation mix was used to transfect competent E. coli strain BMH 71-18, plated with BCIG and IPTG, and a clone containing the complete PstI-KpnI insert was identified.

5. The three cloned blocks were excised from 10 ug double-stranded replicative form of the thee M13 vectors, by digestion with PstI/KpnI (block PK1-5), KpnI (block KKI-5) and KpnI/EcoRI (block KE1-8). The inserts were separated from the vector by electrophoresis on a 20×20 cm 12% polyacrylamide gel, eluted from the gel slices with 0.5 M NH$_4$OAc, 10 mM Mg (OAc)$_2$, 0.1 mM EDTA, 0.1% SDS, and purified by phenol extraction and ethanol precipitation. All three fragments were ligated to PstI/EcoRI cut M13-mp19. 200 white plaques were transferred by toothpick to a fresh 2×TY plate, and grown as a grid of infected colonies. The plate was blotted with nitrocellulose filters, which were then treated with 0.5 M NaOH, followed by 1M Tris-Cl (pH7.5), and baked 1 hr at 80° C. under vacuum. The filters were washed at 67° C. in 3×Denhardt's solution, 2×SSC, 0.07% SDS, followed by 6×SSC at room temperature. Filters were then probed with the radiolabeled olignucleotides KK3 or KK4 in 3 ml of 6×SSC at 37°. Following hybridization with both olignucleotides, positive colonies were picked for DNA sequencing. A phage clone containing correctly assembled blocks was designated M13-HuVLLYS°.

6. To introduce the HuVLLYS° gene in place of the heavy chain variable domain in the vector M13-MOVHNP (described in reference 5) as MV$_{NP}$ with HindII site at the 3' end of the reading frame), double-stranded replicative form DNA of phages M13-HuVLLYS° and M13-MOVHNP were prepared and digested with PstI and BamHI. The insert of M13-HuVLLYS was isolated on a polyacrylamide gel, and the vector portion of M13-MOVHNP was isolated on an agarose gel. The purified fragments were ligated and transfected into E. coli strain BMH71-18, and the resulting plaques probed with oligonucleotide KK3 to identify the insert. The clone was designated M13-HuVLLYS*.

7. In the M13-HuVLLYS* gene, to join the signal sequence of MOVHNP correctly to the 5' end of the HuVLLYS° gene (at the PstI site), single stranded DNA was prepared and altered by oligonucleotide directed mutagenesis with the primer PKO- see paragraph (3) for sequence. The mutant clone was designated M13-HuVLLYS.

Figure 5:
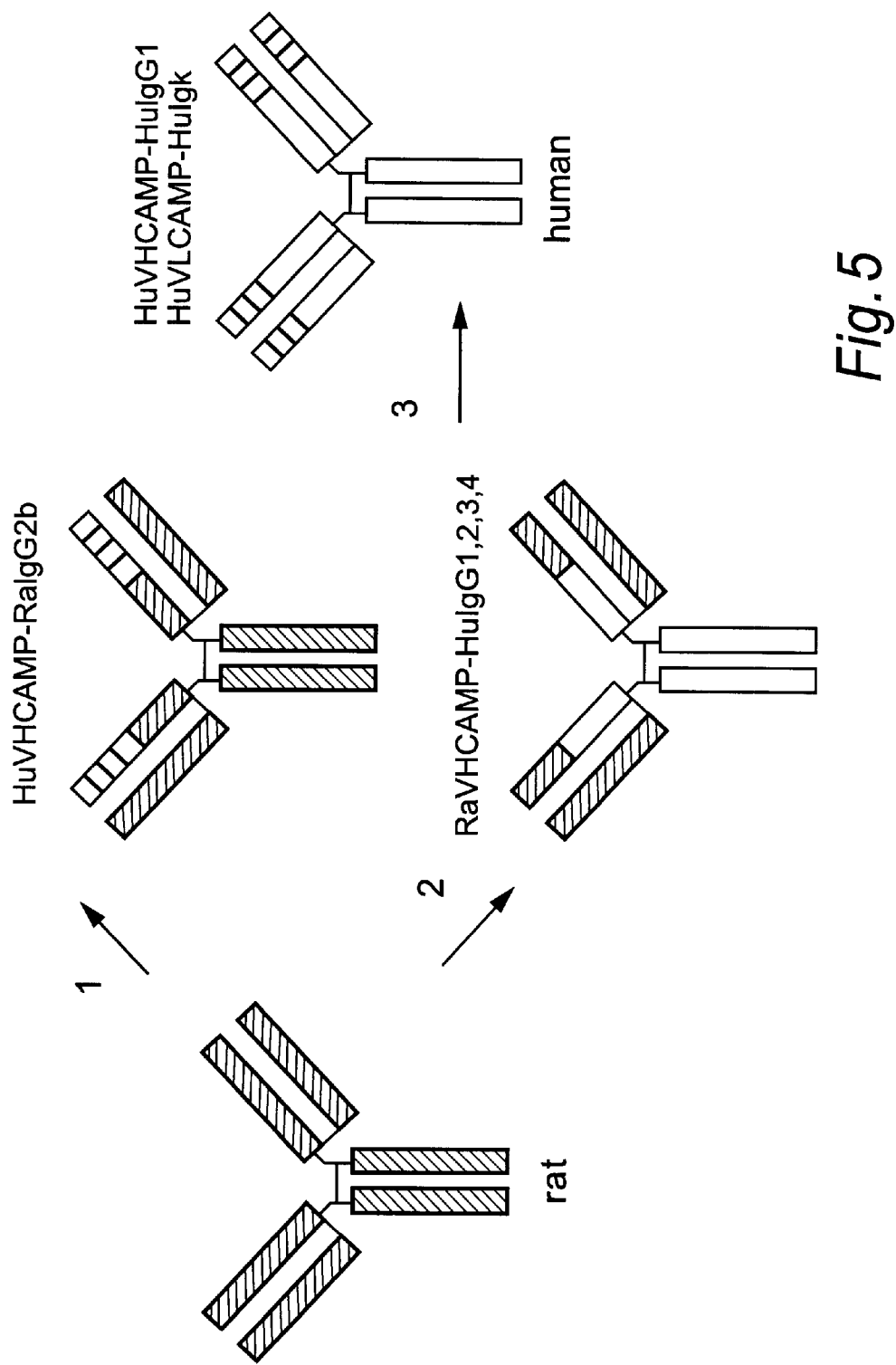
FIG. 5 illustrates a strategy for producing a reshaped human antibody having rat CDRS.

The reshaped human heavy and light chain variable domains were then assembled with constant domains in three stages as illustrated in FIG. 5. In FIG. 5 sequences of rat origin are marked in black, and those of human origin in white. The recombinant heavy and light chains are also marked using a systematic nomenclature.

The illustrated procedure permits a step-wise check on the reshaping of the heavy chain variable domain (stage 1), the selection of the human isotype (stage 2), and the reshaping of the light chain variable domain and assembly of human antibody (stage 3). The vector constructions were genomic, with the variable domains excised from the M13 vectors and cloned as HindIII-BamHI fragments and the constant domains as BamHI-BamHI fragments in either psvgpt (heavy chain) (reference 15) or pSVneo (light chain). (reference 16) vectors. The heavy chain enhancer was included to the 5' side of the variable domain, and expression of both light and heavy chains was driven from heavy chain promoter and the heavy chain signal sequence.

The human gamma 1 (reference 26), gamma 2 (reference 27), gamma 3 (reference 28), gamma 4 (reference 21) and K (reference 22) constant domains, and the rat gamma 2b (reference 29) constant domains were introduced as BamHI- BamHI fragments. The following plasmids were constructed and transfected into lymphoid cell lines by electroporation (reference 30). In stage 1, the pSVgpt vectors HuVHCAMP-RaIgG2B, and also two mutants for reasons. to be explained below, HuVHCAMP(Ser27 to Phe)-RaIgG2B, HuVHCAMP(Ser27 to Phe, Ser30 to Thr)-RaIgG2B) were introduced into the heavy chain loss variant of YTH34.5HL. In stage 2, the pSVgpt vectors RaVHCAMP-RaIgG2B, RaVHCAMP-HuIgG1, RaVHCAMP-HuIgG2, RaVHCAMP-HuIgG3, RaVHCAMP-HuIgG4 were transfected as described above. In stage 3, the pSV-gpt vector Hu(Ser27-Phe, Ser30-Thr)VHCAMP-HuIgGl was cotransfected with the pSV-neo vector HuVLCAMP-HuIgK into the rat myeloma cell line Y0 (Y B2/3.0 Ag 20) (ref. 17). In each of the three stages, clones resistant to mycophenolic acid were selected and screened for antibody production by ELISA assays. Clones secreting antibody were subcloned by limiting dilution (for Y0) or the soft agar method (for the loss variant) and assayed again before 1 liter growth in roller bottles.

Heavy Chain Variable Domain

In stage 1, the reshaped heavy chain variable domain (HuVHCAMP) was attached to constant domains of the rat isotype IgG2b and transfected into a heavy chain loss variant of the YTH34.5 hybridoma. The loss variant carries two light chains, one derived from the Y3 fusion. partner (reference 17). The cloned rat heavy chain variable domain (RaVHCAMP) was also expressed as above.

Antibodies were harvested at stationary phase and concentrated by precipitation with ammonium sulphate, followed by ion exchange chromatography on a Pharmacia MonoQ column. The yields of antibody were measured by an ELISA assay directed against the rat IgG2b isotype, and each adjusted to the same concentration (reference 21).

The HuVHCAMP and RaVHCAMP antibodies—all of the rat IgG2b isotype—were compared in a direct binding assay to the Campath-1 antigen (obtained from a glycolipid extract from human spleen), and also in complement lysis of human lymphocytes. For measuring the binding to antigen, the partially purified Campath-1 antigen was coated onto microtitre wells. Bound antibody was detected via a biotin labelled anti-rat IgG2b monoclonal antibody (reference 21), developed with a streptavidin-peroxidase conjugate (Amersham plc). Complement lysis of human lymphocytes with human serum as the complement source was as described in reference 7. For both binding and complement assays, the titres for the antibodies were determined by fitting the data to a sigmoid curve by a least squares iterative procedure (reference 7), and the concentration of antibody giving 50% maximal binding or lysis was noted.

The results are given in Table 1.

TABLE 1

Reshaping the heavy chain variable domain

| heavy chain variable domain | Concentration of antibody in µg/ml at 50% binding or lysis | |
| --- | --- | --- |
| | antigen binding | complement lysis |
| RaVHCAMP | 0.7 | 2.1 |
| HuVHCAMP | 27.3 | (*) |
| HuVHCAMP (Ser27 to Phe) | 1.8 | 16.3 |
| HuVHCAMP (Ser27 to Phe, Ser30 to Thr) | 2.0 | 17.6 |

(*) Complement lysis with the HuVHCAMP variable domain too weak for the estimation of lysis titre.

Compared with the original rat antibody, or the engineered equivalent, the antibody with the reshaped heavy chain domain HuVHCAMP bound poorly to the Campath-1 antigen and was weakly lytic. This suggested an error in the design of the reshaped domain.

There are several assumptions underlying the transfer of hypervariable loops from one antibody to another, and in particular that the antigen binds mainly to the hypervariable regions. These are defined as regions of sequence (reference 11) or structural (reference 18) hypervariability, and the locations of hypervariable regions are similar by either criterion, except for the first hypervariable loop of the heavy chain. By sequence the first hypervariable loop extends from residues 31 to 35 (reference 11) and by structure from residues 26 to 32 (reference 18). Residues 29 and 30 to form part of the surface loop, and residue 27 which is phenylalanine or tyrosine in most sequences including YTH34.5HL, helps pack against residues 32 and 34.

By way of illustration, see FIG. 6 which illustrates loop Phe27 to Tyr35 in the heavy chain variable domain of the human myeloma protein KOL which is crystallographically solved (reference 31). The backbone of the hypervariable region according to Kabat (reference 11) is highlighted, and a 200% van der Waal surface is thrown around Phe27 to show the interactions with Tyr32 and Met34 of the Kabat hypervariable region. In the rat YTH34.5HL heavy chain, these three side chains are conserved, but in HuVHCAMP, Phe27 is replaced by Ser: this is because, unlike most human heavy chains, in NEW the phenylalanine is replaced by serine, which would be unable to pack in the same way as phenylalanine. To restore the packing of the loop, a Ser(27) to Phe mutation was made in HuVHCAMP, and also a double mutation Ser(27) to Phe, Ser(30) to Thr (as mentioned above).

The two mutants showed a significant increase in binding to CAMPATH-1 antigen and lysed human lymphocytes with human complement. See the results given in Table 1. Thus the affinity of the reshaped antibody could be restored by altering the packing between the hypervariable regions and the framework by a single Ser(27) to Phe mutation. This suggests that alterations in the "Kabat" framework region can enhance the affinity of the affinity of the antibody, and extends previous work in which an engineered change in the hypervariable region yielded an antibody with increased affinity (reference 19).

Heavy Chain Constant Domains

In stage 2 (FIG. 5), the rat heavy chain variable domain was attached to constant domains of the human isotypes IgG1, 2, 3, and 4, and transfected into the heavy chain loss variant of the YTH34.5 hybridoma.

Antibody was harvested from cells in stationary phase, concentrated by precipitation with ammonium sulphate and desalted into phosphate buffered saline (PBS). Antibodies bound to the Campath-1 antigen coated on microtitre plates, were assayed in ELISA directed against the rat k light chain (reference 21), and adjusted to the same concentration. The antibodies were assayed in complement lysis (as described above) and ADCC with activated human peripheral blood mononuclear cells (references 21, 32). Briefly, $5 \times 10^4$ human peripheral blood cells were labelled with $^{51}$Cr and incubated for 30 minutes at room temperature with different concentrations of antibody. Excess antibody was removed and a 20 fold excess of activated cells added as effectors. After 4 hours at 37° C. death was estimated by $^{51}$Cr release.

Figure 7A:
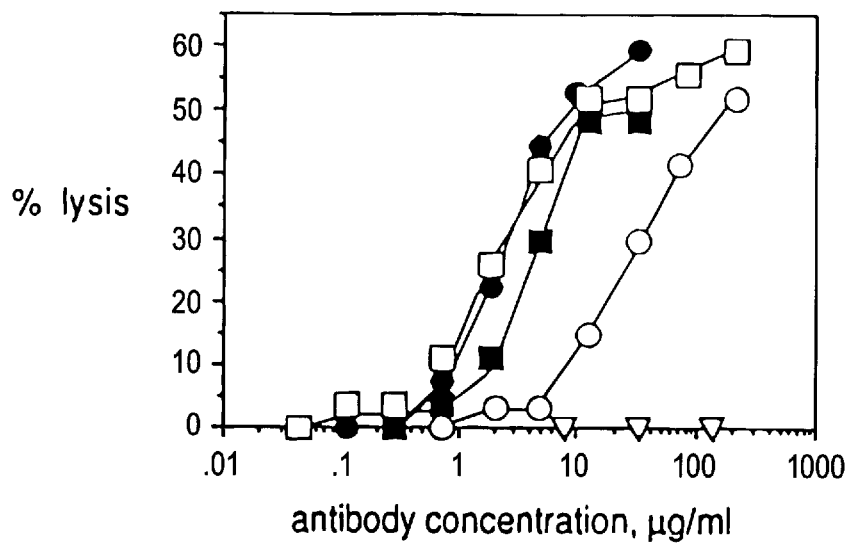
FIGS. 7a and 7b illustrate the results of complement lysis and ADCC for various antibodies.
Figure 7B:
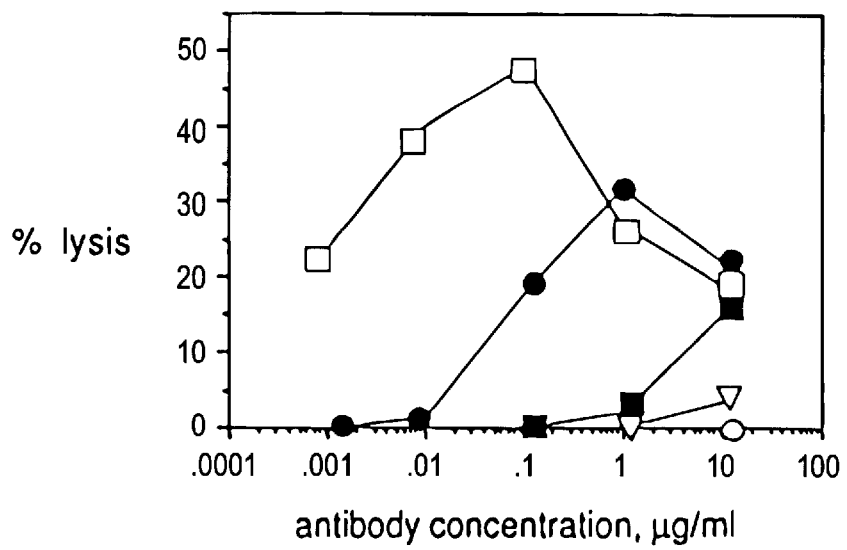

The results are shown in FIG. 7, in which the results for rat heavy chain variable domain attached to different human isotypes are represented as follows:

| | |
|---|---|
| IgG1 | empty squares |
| IgG2 | empty circles |
| IgG3 | solid squares |
| IgG4 | empty triangles |

Results of lysis with the antibody YTH34.5HL are represented by solid circles.

In complement lysis (FIG. 7a), the human IgG1 isotype proved similar to the YTH34.5HL-G2b, with the human IgG3 isotype less effective. The human IgG2 isotype was only weakly lytic and the IgG4 isotype non-lytic. In ADCC (FIG. 7b) the human IgG1 was more lytic than the YTH34.5HL-G2b antibody. The decrease in lysis at higher concentration of the rat IgG2b and the human IgG1 antibody is due to an excess of antibody, which causes the lysis of effector cells. The human IgG3 antibody was weakly lytic, and the IgG2 and IgG4 isotypes were non-lytic.

The human IgG1 isotype was therefore suitable for a reshaped antibody for therapeutic use. Other recent work also suggests the IgG1 isotype as favoured for therapeutic application. When the effector functions of human isotypes were compared using a set of chimaeric antibodies with an anti-hapten variable domain, the IgG1 isotype appeared superior to the IgG3 in both complement and cell mediated lysis (reference 4). Furthermore, of two mouse chimaeric antibodies directed against cell surface antigens as tumour cell markers, with human IgG1 or IgG3 isotypes, only the IgG1 isotype mediated complement lysis (references 2, 3).

Light Chain

In stage 3 (FIG. 5), the reshaped heavy chain was completed, by attaching the reshaped HuVHCAMP (Ser27 to Phe, Ser30 to Thr) domain to the human IgG1 isotype. The reshaped light chain domain HuVHCAMP was attached to the human Ck domain. The two vectors were cotransfected into the non-secreting rat Y0 myeloma line.

Antibody HuVHCAMP (Ser27 to Phe, Thr30 to Ser)-HuIGG1, HuVLCAMP-HuIGK was purified from supernatants of cells in stationary phase by affinity chromatography on protein A Sepharose. The antibody was at least 95% (by wt) pure. The yield (about 10 mg/l) was measured spectrophotometrically. Complement and ADCC assays were performed as described in connection with FIG. 7.

The results are shown in FIG. 8, in which the results are reshaped human antibodies are represented by squares and those for rat YTH34.5HL antibodies are represented by solid circles.

Figure 8A:
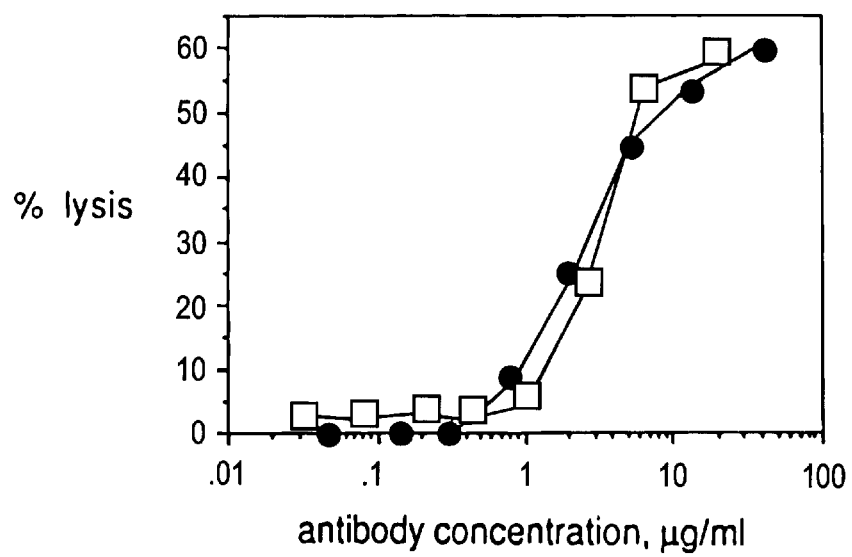
FIGS. 8a and 8b illustrate the results of complement lysis and ADCC of various further antibodies.
Figure 8B:
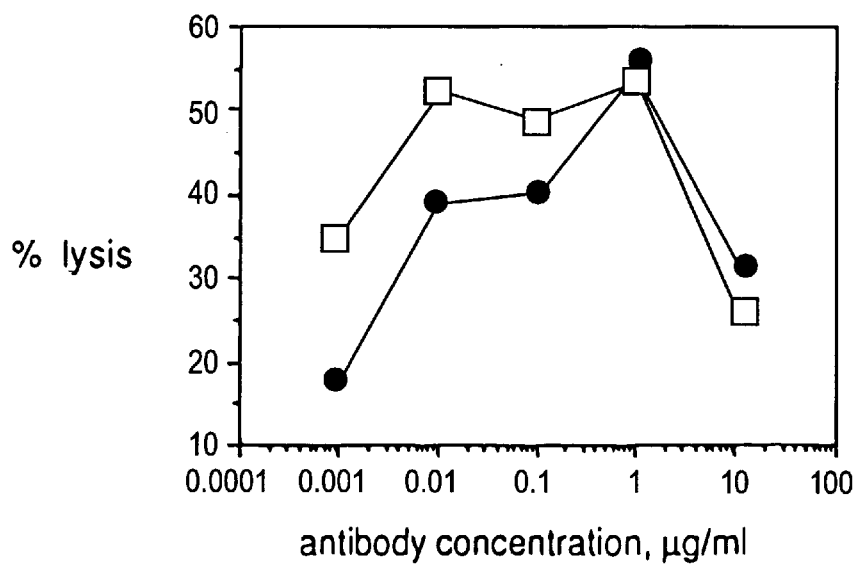

The purified antibody proved almost identical to the YTH34.5HL-G2b antibody in complement lysis (FIG. 8a). In cell mediated lysis the reshaped human antibody was more reactive than the rat antibody (FIG. 8b). Similar results to the ones in FIG. 8b were obtained with three different donors of target and effector cells (data not shown). Furthermore the antibody was as effective as YTH34.5HL-G2b in killing leukaemic cells from three patients with B Cell lymphocytic leukaemia by complement mediated lysis with human serum.

The rat antibody and fully humanised antibody were compared in a direct binding assay to Campath-1 antigen. Antibody concentrations were determined as described in FIGS. 7 and 8. The amount of rat antibody bound to partially purified Campath-1 antigen was determined as described in connection with Table 1. The amount of human antibody bound was determined by an ELISA assay using a biotinylated sheep anti-human IgG antibody (Amersham).

TABLE 2

Reshaping the heavy and light chain variable domains simultaneously

| antibody | Concentration of antibody in μg/ml at 50% binding antigen binding |
|---|---|
| RaVHCAMP Ra1GG2B | |
| RaVHCAMP RaKappa | 1.01 |
| HuVHCAMP (Ser 27 to Phe, Ser30 to Thr) | |
| Hu1GG1 | |
| HuVLCAMP HuKappa | 1.11 |

Thus by transplanting the hypervariable regions from a rodent to a human antibody of the IgG1 subtype, the antibody can be reshaped for therapeutic application.

The strategy illustrated in FIG. 5 is stepwise assembly to allow any problems to be detected at each stage (reshaping of heavy chain variable domain, selection of constant domain and reshaping of light chain variable domain). It is quite possible to build the reshaped antibody in a single step assembly, i.e. constructing the two reshaped variable domains, attaching to appropriate constant domains and cotransfecting into e.g. Y0.

EXAMPLE 2

Patients and Methods

Antibody HuVHCAMP (Ser 27 to Phe, Thr 30 to Ser)— HuIGG1, HuVLCAMP—HuIGK, hereinafter referred to as CAMPATH-1H, was prepared as described in Example 1. The CAMPATH-1H antibodies were obtained from culture supernatant of cells growing in a hollow fibre bioreactor ('Acusyst—Jr', Endotronics) and purified by affinity chromatography on protein-A-'sepharose'. They were dissolved in phosphate-buffered saline, sterile filtered, and tested for pyrogen and sterility. Patients were prehydrated over night and antibody, diluted in 500 ml saline, was infused over 2–4 hours.

Campath-1 expression on tumour cells was measured by flow cytometry and complement-mediated lysis (references 6, 35). Serum concentrations of CAMPATH-1H were measured by immunofluorescence with normal lymphocytes. Southern blot analysis with an immunoglobulin $J_H$ probe was used to detect residual tumour cells in DNA extracted from mononuclear fractions of bone marrow. Antiglobulin responses were sought by two techniques. The first was a solid-phase enzyme-linked assay using microliter plates coated with CAMPATH-1H. After incubation with patients' serum samples, the assay was developed with biotin-labelled CAMPATH-1H followed by streptavidin-peroxidase. A mixture of monoclonal mouse antibodies against human IgG was used as a positive control and 500 ng/ml of this mixture would be detected. In the second assay, patients serum samples were mixed with red cells coupled with CAMPATH-1H (reference 10). Agglutination by 5 ng/ml of the control mixture would be detected. Immunoglobulin allotypes were determined by means of standard reagents and techniques from the Central Laboratory of the Netherlands Red Cross Blood Transfusion Service.

Results

Patient 1

A 69-year-old woman presented in 1983, and grade 1, stage IVA non-Hodgkin lymphoma in leukaemic phase was diagnosed. Between 1983 and 1988 the patient received various types of treatment, including chemotherapy and radiotherapy and rat antibody to Campath-1. She was then given treatment with CAMPATH-1H.

Figure 9:
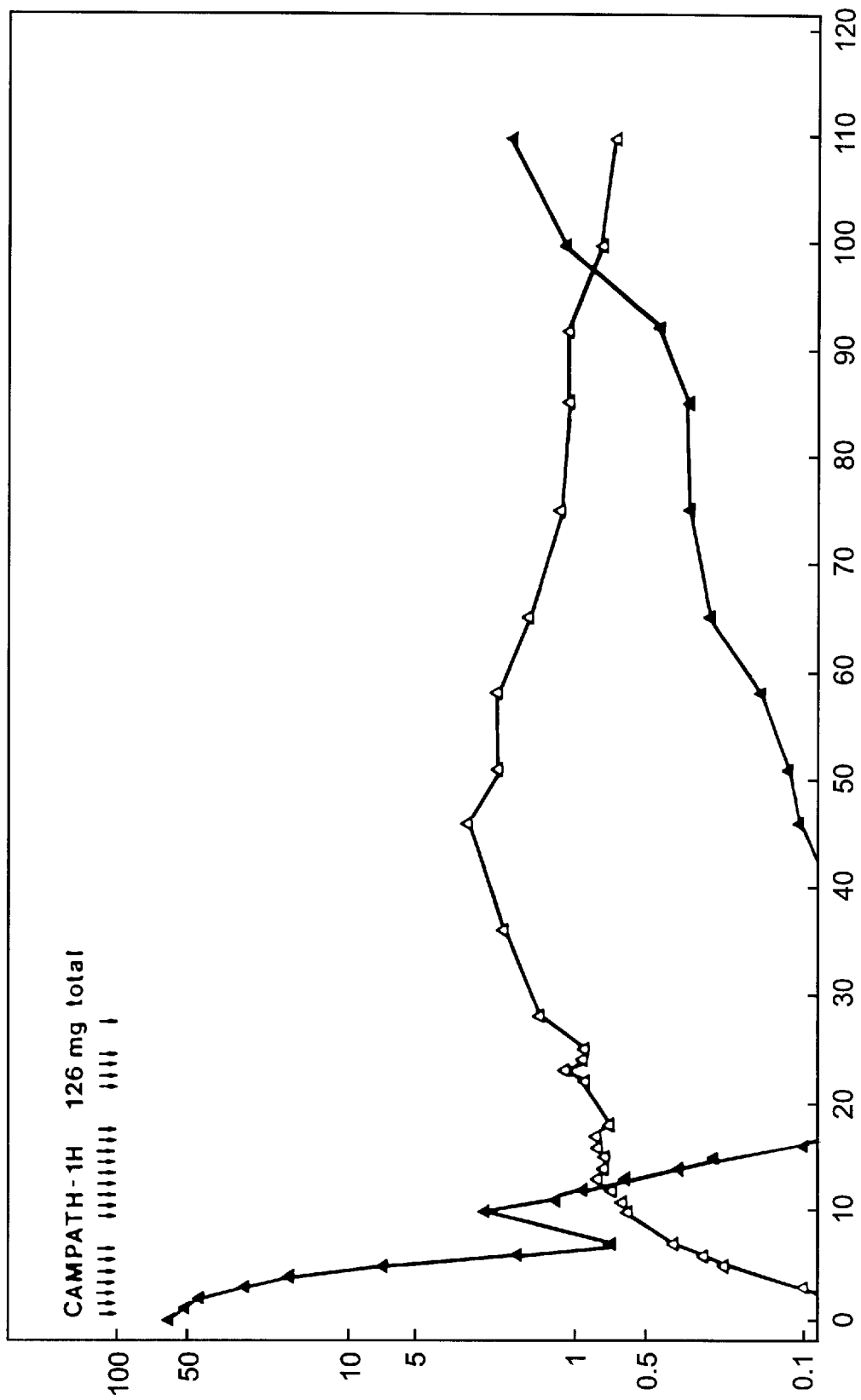
FIG. 9 shows the effect of CAMPATH-1H on blood counts in a patient (patient 1), with solid triangles showing results for lymphocytes and empty triangles results for neutrophils.

The starting dose was 1 mg daily and, since it was well tolerated, the dose was increased to a maximum of 20 mg/day, though the usual was 4 mg/day owing to the small amount available. In all the patient received 126 mg over 30 days. The response was prompt; in 6 days night sweats had abated, by day 10 there was pronounced reduction in splenomegaly and recovery of blood neutrophils, and by day 18 lymphoma cells were cleared from the blood (FIG. 9).

On day 28 a bone marrow aspirate and trephine were hypocellular but showed active myelopoiesis and erythropoiesis and no lymphoid cells (FIG. 10B). No CAMPATH-1 positive cells could be detected by flow cytometry. DNA from the mononuclear marrow cells was germline when probed with an immunogloublin $J_H$ probe under conditions where clonal rearrangements could be detected in 0.2% of cells.. Thus, it is concluded that lymphoma cells were cleared from the marrow. The spleen volume was reduced about eight-fold (FIGS. 11A, B), although it was still slightly larger than normal.

Other than fever occurring about 1 hour after the end of antibody infusions there were no adverse effects of antibody treatment until the 5th week, when severe rigors occurred after each infusion. No antiglobulin response could be detected and the rate of clearance of antibody from the serum was unchanged. For the next 3 weeks the patient continued to experience occasional fever and rigors. She was given oral. cotrimoxazole because of her lymphopenia, but no infective cause of these symptoms could be found.

In the next 4 months lymphocytes, which appeared morphologically normal, slowly reappeared in the blood (up to $0.2 \times 10^9/l$). They did not show the characteristic rearranged immunogloublin fragments, and both CD3-positive and CD19-positive cells were present (see Table 3). Serum immunoglobulin levels, which had been very low since presentation, have risen towards normal (Table 3). A marrow aspirate and trephine taken 50 days after the end of treatment were again hypocellular but had no lymphomatous infiltration. This marrow sample contained 4% CAMPATH-1-positive cells and showed some oligoclonal rearrangements of immunoglobulin genes. However, by day 100, lymphoma cells were again detected in the blood and the spleen size had started to increase. A second course of 12 days' therapy with CAMPATH-1H was completed with similar therapeutic benefit to the first and no adverse effects. Since the main resevoir of disease in the patient appeared to be the spleen, splenectomy was carried out at the end of this second course of treatment. At that time no tumour cells could be detected in blood or marrow. The patient is now well 37 days after the splenectomy. The lymphocyte count is low but she has normal neutrophil, platelet, and red-cell counts.

Patient 2

Figure 11A:
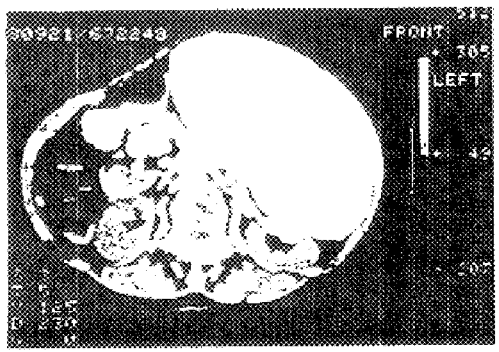
Figure 11B:
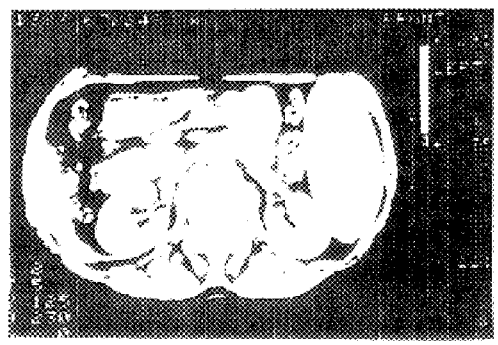
Figure 11C:
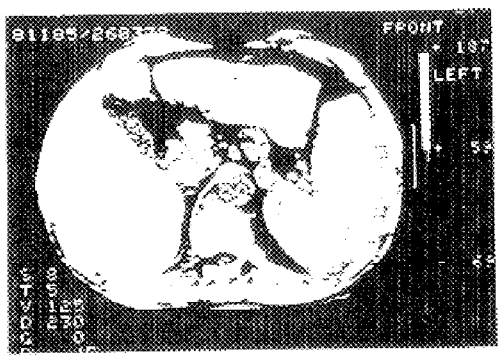

A 67-year old man presented in April 1988 with splenic pain; there was 12 cm splenomegaly, and computed tomography scan of thorax and abdomen revealed retrocrural and para-aortic lymphadenopathy, the largest node measuring 3 cm in diameter (FIG. 11C). A blood count revealed $36.6 \times 10^9$ lymphocytes/ml, the majority being lymphoplasmacytoid cells which expressed surface IgG-kappa and were characterised by large cytoplasmic periodic-acid-Schiff-positive vacuoles which could be intensely stained by anti-IgG. A marrow aspirate contained 72% lymphomatous cells (FIG. 10C). DNA from blood mononuclear cells showed biallelic rearrangement of immunoglobulin $J_H$ genes but was germline with various T-cell receptor and oncogene probes. The lymphoma cells expressed the CAMPATH-1 antigen in amounts comparable with normal lymphocytes but were more resistant to complement-mediated lysis. Stage IVA grade I lymphoplasmacytoid non-Hodgkin lymphoma was diagnosed.

Figure 11D:
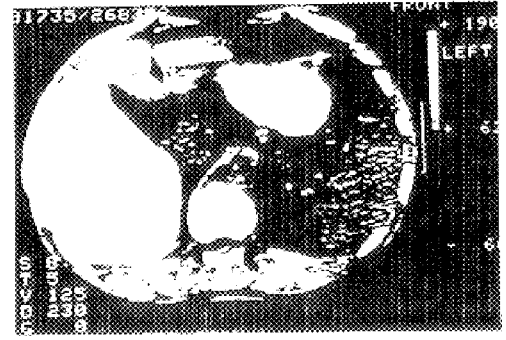

The patient was offered CAMPATH-1H as primary therapy and received a total of 85 mg over 43 days. This resulted in clearance of the lymphoma cells and normal lymphocytes from blood (FIG. 12) and marrow (FIG. 10D), resolution of splenomegaly, and improvement in the lymphadenopathy. A computed tomography scan taken 8 days after the end of antibody treatment was normal (FIG. 11D). A bone marrow aspirate taken at the same time showed active haemopoiesis but no lymphoma cells, and no CAMPATH-1-positive cells could be detected by flow cytometry. DNA from the mononuclear fraction of this marrow showed only germline configuration when probed with the immunoglobulin $J_H$ probe. By day 78 morphologically normal blood lymphocytes began to reappear and none of the vacuolated cells could be seen. The patient remains well and off therapy.

Some toxic effects of CAMPATH-1H were observed. The first dose was stopped after 3 mg had been given because of hypotension, possibly caused by tumour lysis. This problem was subsequently avoided by giving smaller doses at a slower rate and when lymphoma cells had been cleared from the blood, the dose was increased to a maximun of 8 mg over 4 h without any effect on blood pressure. Nevertheless, all doses induced fever (up to 38.5° C.), and malaise for up to 36 h, but these were not severe enough to stop antibody treatment which, after the first week, was given on an outpatient basis. Treatment was stopped after 43 days because of the development of an urticarial rash after two successive antibody infusions.

Half-life of CAMPATH 1-H

The concentration of CAMPATH-1H was measured in serum samples taken before and after antibody infusions and at other times throughout treatment. In theory, a dose of 4–6 mg corresponds to about 1 ug/ml in the plasma. In fact free antibody could not be detected until day 4–6, about 5–20% after 24 hours.

Lack of Antiglobulin Response

The allotype of CAMPATH-1H is Glm(1,2,17),Km(3). Patient 1 was Glm(1,3,17),Km(3) and patient 2 was Glm (3),Km(3), so both could theoretically have made an anti-allotype response as well as a response to the hypervariable regions. However, we failed to detect any antiglobulin to CAMPATH-1H either by the solid-phase enzyme-linked assay or by the more sensitive haemagglutination assay. In addition, the rate of clearance of CAMPATH-1H did not change and free antibody could be detected for up to 8 days after the last dose had been given. It is possible that the reactions experienced at the end of the course of treatment could have been provoked by contaminating non-human proteins in the antibody preparation.

Discussion

The remissions achieved in these two patients show that it is possible to clear large numbers of tumour cells with small amounts of an unmodified monocclonal antibody. The effects in the first patient were far superior to the results of the previous chemotherapy and radiotherapy. The selective lysis of lymphoma cells with recovery of normal haemopoiesis during the course of treatment was an important advantage, which allowed treatment to be given largely on an outpatient basis. It is believed the choice of antibody-specificity and isotype is important; indeed, it may be why these tests had more success than previous efforts with other monoclonal antibodies. (References 36–38.) The CAMPATH-1 antigen seems to be a good target because it is widely distributed and abundant, and does not suffer from antigenic modulation. (References 6,35.)

TABLE 3

PATIENT CHARACTERISTICS BEFORE AND AFTER TREATMENT WITH CAMPATH-1H

| Diagnosis | | Case 1 Stage IVB grade I NHL in leukaemic phase | | Case 2 Stage IVA grade I lymphoplasma-cytoid NHL | |
|---|---|---|---|---|---|
| | | before | after | before | after |
| Spleen size | ml | 4460 | 590 | 2600 | 440 |
| Lymphadenopathy | | nil | nil | retrocrural paraortic | nil |
| Bone marrow | | | | | |
| lymphoma cell | % | 99 | 0 | 72 | 0 |
| Southern blot analysis | | | | | |
| Ig $J_H$ fragment | | R/R | G/G | R/R | G/G |
| Peripheral blood | | | | | |
| haemoglobin | g/dl | 8.7 | 10.6 | 11.2 | 12.0 |
| reticulocytes | $\times 10^9/l$ | 31 | 135 | nd | nd |
| platelets | $\times 10^9/l$ | 37 | 50 | 110 | 453 |
| lymphocytes | $\times 10^9/l$ | 60 | 0 | 37 | 0 |
| neutrophils | $\times 10^9/l$ | 0 | 2.0 | 4.6 | 7.3 |
| monocytes | $\times 10^9/l$ | 0 | 0.04 | 1.5 | 0.5 |
| Lymphocyte phenotype | | | | | |
| CD19 | % | 97 | 46 | 93 | <5 |
| CD3 | % | 0 | 32 | 8 | 80 |
| CAMPATH-1M | % | 96 | nd | 95 | nd |
| CAMPATH-1H | % | 98 | nd | 97 | nd |
| Serum immunoglobulins | | | | | |
| IgM | g/l | <0.3 | 1.2 | <0.3 | 0.7 |
| IgA | g/l | <0.5 | <0.5 | <0.5 | 0.5 |
| IgG | g/l | 5.8 | 8.2 | 3.2 | 4.7 |
| Bence-Jones | | nil | nil | ++ | nil |

The post-therapy values refer to measurements made shortly after the end of antibody therapy, except for lymphocyte phenotyping and serum Ig, which were assessed 6 weeks later. Lymphocyte phenotypes were measured by immunofluorescence and APAAP techniques. Spleen and lymph node dimensions were measured by serial CT scanning (FIG. 11). nd=not done

REFERENCES

1. Neuberger, M. S., Williams, G. T., Mitchell, E. B., Jouhal, S. S., Flanagan, J. G. & Rabbits, T. H. Nature 314, 268–270 (1985).
2. Liu, A. Y., Robinson, R. R., Hellstrom, K. E., Murray, E. D. Jr., Cheng, C. P. & Hellstrom, I. Proc.natl.Acad.Sci USA 84,3439–3443 (1987).
3. Shaw, D. R., Khazaeli, M. B., Sun, L. K., Ghraeyeb, J., Daddona, P. E., McKinney, S. & Lopuglio, A. F. J, Immunol. 138,4534–4538 (1987).
4. Bruggemann, M., Williams, G. T., Bindon, C., Clark, M. R., Walker, M. R., Jefferis, R., Waldmann, H. & Neuberger, M. S. J.Exp.Med. 166, 1351–1361 (1987).
5. Jones, P. T., Dear, P. H., Foote, J., Neuberger, M. S. & Winter, G. Nature 321,522–525 (1986).
6. Hale, G., Bright, S., Chumbley, G., Hoang, T., Metcalf, D., Munro, A. J. & Waldmann, H. Blood 62,873–882 (1983).
7. Hale, G., Hoang, T., Prospero, T., Watts, S. M. & Waldmann, H. Mol.Biol.Med. 1,305–319 (1983).
8. Hale, G., Cobbold, S. P., Waldmann, H., Easter, G., Matejtschuk, P. & Coombs, R. R. A. J. Immunol.Meth. 103,59–67 (1987).
9. Hale, G., Waldmann, H., Friend, P. & Calne, R. Transplantation 42,308–311 (1986).
10. Hale, G., Swirsky, D. M., Hayhoe, F. G. J. & Waldmann, H. Mol.Biol.Med. 1,321–334 (1983).
11. Kabat, E. A., Wu, T. T., Reid-Miller, M., Perry, H. M. & Gottesman, K. S. in Sequences of Proteins of Immunological Interest (US Dept. of Health and Human Services, 1987).
12. Chothia, C., Novotny, J., Bruccoleri, R. & Karplus, M. J. Mol.Biol. 186,651–663 (1985).
13. Saul, F. A., Amzel, M. & Poljak, R. J. J.Biol.Chem. 253,585–597 (1978).
14. Epp, O., Colman, P., Fehlhammer, H., Bode, W., Schiffer, M. & Huber, R. Eur.J.Biochem. 45,513–524 (1974).
15. Mulligan, R. C. & Berg, P. Proc.natl.Acad.Sci USA 78,2072–2076 (1981).
16. Southern, P. J. & Berg, P. J. Mol.Appl.Genetics 1,327–341 (1981).
17. Galfre, G. & Milstein, C. Meth.Enzymol. 73,1–46 (1981).
18. Chothia, C. & Lesk, A. J.Mol.Biol. 196,901–917 (1987).
19. Roberts, S., Cheetham, J. C. & Rees, A. R. Nature 328,731–734 (1987).
20. Jonker, M. & den Brok, J. H. A. M. Eur.J. Immunol. 17, 1547–1552 (1987).
21. Clark, M. & Waldmann, H. J.N.C.I. 79, 1393–1398 (1987).
22. Hieter, P. A., Max, E. E., Seidmann, J. G., Maizel, J. V. Jr & Leder, P. Cell 22,197–207 (1980).
23. Kaartinen, M., Griffiths, G. M., Hamlyn, P. H., Markham, A. F., Karjalainen, K., Pelkonen J. L. T., Makela, O. & Milstein, C. J. Immunol. 130,320–324 (1983).
24. Gubler, U. & Hoffmann, B. J. Gene 25,263–269 (1983).
25. Sanger, F., Nicklen, S. A. & Coulson, A. R. Proc.natl.Acad.Sci USA 74,5463–5467 (1977).
26. Takahashi, N., Ueda, N. S., Obata, M., Nikaido, T. Honjo, T. Cell 29,671–679 (1982).
27. Flanagan, J. G. & Rabbits, T. H. Nature 300,709–713 (1982).
28. Huck, S., Fort, P., Crawford, D. H., Lefranc, M.-P. & Lefranc, G. Nucl.Acid Res. 14,1779–1789 (1986).
29. Bruggemann, M., Free, J., Diamond, A., Howard, J., Cobbold, S. & Waldmann, H. Proc.natl.Acad.Sci. USA 83,6075–6079 (1986).
30. Potter, H., Weir, L. & Leder, P. Proc.natl.Acad.Sci. USA 81,7161–7163 (1984).
31. Marquardt, M., Deisenhofer, J.,Huber, R. & Palm, W. J.Mol.Biol. 141,368–391 (1980).
32. Hale, G., Clark, M. & Waldmann, H. J. Immunol. 134,3056–3061 (1985).
33. Carter, P., Bedouelle, H. & Winter, G. Nucleic Acids Res. 13,4431–4443 (1985).
34. Heiter, P., Maizel, J & Leder, P. J. Biol. Chem. 257, 1516–1522 (1982).
35. Hale, G., Swirsky, D., Waldman, H., & Chan, L. C., Br. J. Haematol. 60, 41–48, (1985).
36. Ritz. J., Schlossman, S. F., Blood, 59, 1–11 (1982).
37. Levy. R., Miller R. A., Annu. Rev. Med., 34, 107–16 (1983).
38. Stevenson, G. T., Glennie, M. J., Cancer Surv. 4, 213–44, (1985).

What is claimed is:

1. An antibody which binds effectively to the antigen Campath-1, said antibody comprising a constant region of human origin, heavy and light chain variable domain framework regions which are of human origin, and complementarity determining regions defined by amino acid residues 31 to 35, 50 to 65 and 95 to 102 of the heavy chain as shown in FIG. 2a, and amino acid residues 24–34, 50–56 and 89–97 of the light chain as shown in FIG. 2b.

2. The antibody of claim 1, wherein the constant region is of the IgG class.

3. A composition for administration to patients comprising an antibody which binds effectively to the antigen Campath-1 and a physiologically acceptable diluent or carrier, said antibody comprising a constant region of human origin, heavy and light chain variable domain framework regions which are of human origin, and complementarity determining regions defined by amino acid residues 31 to 35, 50 to 65 and 95 to 102 of the heavy chain as shown in FIG. 2a, and amino acid residues 24–34, 50–56 and 89–97 of the light chain as shown in FIG. 2b.

4. The composition of claim 3, wherein the constant region is the IgG class.

5. A method of treating a human patient having a lymphoid malignancy, comprising administering to said patient an antibody which binds effectively to the antigen Campath-1, said antibody comprising a constant region of human origin, heavy and light chain variable domain framework regions which are of human origin, and complementarity determining regions defined by amino acid residues 31 to 35, 50 to 65 and 95 to 102 of the heavy chain as shown in FIG. 2a, and amino acid residues 24–34, 50–56 and 89–97 of the light chain as shown in FIG. 2b.

6. The method of claim 5, wherein the constant region is of the IgG class.

7. A method for treating a human patient having a lymphoid malignancy, comprising administering to said patient an antibody which binds effectively to the antigen Campath-1, said antibody comprising a light chain variable domain containing amino acid residues 1 to 108 as identified in the upper lines of sequence information in FIG. 2b, a heavy chain variable domain containing amino acid residues 1 to 26, 28, 29 and 31 to 113, as identified in the upper lines of sequence information in FIG. 2a, wherein residue 27 of said heavy chain variable domain is phenylalanine, and heavy chain constant regions of human origin of the IgG class.

8. A method for treating a human patient having a lymphoid malignancy, comprising administering to said patient an antibody which binds effectively to the antigen Campath-1, said antibody comprising a light chain variable domain containing amino acid residues 1 to 108 as identified in the upper lines of sequence information in FIG. 2b, a heavy chain variable domain containing amino acid residues 1 to 26, 28, 29 and 31 to 113, as identified in the upper lines of sequence information in FIG. 2a, wherein residue 27 of said heavy chain variable domain is phenylalanine and residue 30 of said heavy chain variable domain is threonine, and heavy chain constant regions of human origin of the IgG class.

9. The method of claim 7, wherein the patient has a lymphoma.

10. The method of claim 8, wherein the patient has a lymphoma.

11. The method of claim 7, wherein the heavy chain constant regions are of the IgG$_1$ type.

12. The method of claim 8, wherein the heavy chain constant regions are of the IgG$_1$ type.

13. An isolated DNA molecule comprising a sequence encoding an antibody which binds effectively to the antigen Campath-1, said antibody comprising a constant region of human origin, heavy and light chain variable domain framework regions which are of human origin, and complementarity determining regions defined by amino acid residues 31 to 35, 50 to 65 and 95 to 102 of the heavy chain as shown in FIG. 2a, and amino acid residues 24–34, 50–56 and 89–97 of the light chain as shown in FIG. 2b.

14. An isolated DNA molecule comprising a sequence encoding an antibody which binds effectively to the antigen Campath-1, said antibody comprising a light chain variable domain containing amino acid residues 1 to 108 as identified in the upper lines of sequence information in FIG. 2b, a heavy chain variable domain containing residues amino acid residues 1 to 26, 28, 29 and 31 to 113, as identified in the upper lines of sequence information in FIG. 2a, wherein the residue 27 of said heavy chain variable domain is phenylalanine, and heavy chain constant regions of human origin of the IgG class.

15. An isolated DNA molecule comprising a sequence encoding an antibody which binds effectively to the antigen Campath-1, said antibody comprising a light chain variable domain containing amino acid residues 1 to 108 as identified in the upper lines of sequence information in FIG. 2b, a heavy chain variable domain containing residues amino acid residues 1 to 26, 28, 29 and 31 to 113, as identified in the upper lines of sequence information in FIG. 2a, wherein the residue 27 of said heavy chain variable domain is phenylalanine and residue 30 of said heavy chain variable domain is threonine, and heavy chain constant regions of human origin of the IgG class.

16. A cell line which expresses an antibody which binds effectively to the antigen Campath-1, said antibody comprising a constant region of human origin, heavy and light chain variable domain framework regions which are of human origin, and complementarity determining regions defined by amino acid residues 31 to 35, 50 to 65 and 95 to 102 of the heavy chain as shown in FIG. 2a, and amino acid residues 24–34, 50–56 and 89–97 of the light chain as shown in FIG. 2b.

17. A cell line which expresses an antibody which binds effectively to the antigen Campath-1, said antibody comprising a light chain variable domain containing amino acid residues 1 to 108 as identified in the upper lines of sequence information in FIG. 2b, a heavy chain variable domain containing residues amino acid residues 1 to 26, 28, 29 and 31 to 113, as identified in the upper lines of sequence information in FIG. 2a, wherein the residue 27 of said heavy chain variable domain is phenylalanine, and heavy chain constant regions of human origin of the IgG class.

18. A cell line which expresses an antibody which binds effectively to the antigen Campath-1, said antibody comprising a light chain variable domain containing amino acid residues 1 to 108 as identified in the upper lines of sequence information in FIG. 2b, a heavy chain variable domain containing residues amino acid residues 1 to 26, 28, 29 and 31 to 113, as identified in the upper lines of sequence information in FIG. 2a, wherein the residue 27 of said heavy chain variable domain is phenylalanine and residue 30 of said heavy chain variable domain is threonine, and heavy chain constant regions of human origin of the IgG class.

* * * * *

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:1:

Asp Phe Tyr Met Asn
1               5

(2) INFORMATION FOR SEQ ID NO:2:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:2:

Phe Ile Arg Asp Lys Ala Lys Gly Tyr Thr Thr Glu Tyr Asn Pro Ser
1               5                   10                  15

Val Lys Gly (2) INFORMATION FOR SEQ ID NO:3:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:3:

Glu Gly His Thr Ala Ala Pro Phe Asp Tyr
1               5                   10

(2) INFORMATION FOR SEQ ID NO:4:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:4:

Lys Ala Ser Gln Asn Ile Asp Lys Tyr Leu Asn
1               5                   10

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:5:

Asn Thr Asn Asn Leu Gln Thr
1               5

(2) INFORMATION FOR SEQ ID NO:6:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:6:

Leu Gln His Ile Ser Arg Pro Arg Thr
1               5

(2) INFORMATION FOR SEQ ID NO:7:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:7:

Glu Val Lys Leu Leu Glu Ser Gly Gly Gly Leu Val Pro Gly Gly Ser
1               5                   10                  15

Met Arg Leu Ser Cys Ala Gly Ser Gly Phe Thr Phe Thr Asp Phe Tyr
                20                  25                  30

Met Asn Trp Ile Arg Gln Pro Ala Gly Lys Ala Pro Glu Trp Leu Gly
            35                  40                  45

Phe Ile Arg Asp Lys Ala Lys Gly Tyr Thr Thr Glu Tyr Asn Pro Ser
        50                  55                  60

Val Lys Gly Arg Phe Thr Ile Ser Arg Asp Asn Thr Gln Asn Met Leu
65                  70                  75                  80

Tyr Leu Gln Met Asn Thr Leu Arg Ala Glu Asp Thr Ala Thr Tyr Tyr
                85                  90                  95

Cys Ala Arg Glu Gly His Thr Ala Ala Pro Phe Asp Tyr Trp Gly Gln
            100                 105                 110

Gly Val Met Val Thr Val Ser Ser
            115                 120

(2) INFORMATION FOR SEQ ID NO:8:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO:8:

Asp Ile Lys Met Thr Gln Ser Pro Ser Phe Leu Ser Ala Ser Val Gly
1               5                   10                  15

Asp Arg Val Thr Leu Asn Cys Lys Ala Ser Gln Asn Ile Asp Lys Tyr
                20                  25                  30

Leu Asn Trp Tyr Gln Gln Lys Leu Gly Glu Ser Pro Lys Leu Leu Ile
            35                  40                  45

Tyr Asn Thr Asn Asn Leu Gln Thr Gly Ile Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Leu Gln His Ile Ser Arg Pro Arg
                85                  90                  95

Thr Phe Gly Thr Gly Thr Lys Leu Glu Leu Lys Arg
            100                 105

(2) INFORMATION FOR SEQ ID NO:9:

(i) SEQUENCE CHARACTERISTICS:
        (A) LENGTH: 122 amino acids
        (B) TYPE: amino acid
        (D) TOPOLOGY: linear (ii) MOLECULE TYPE: protein (xi) SEQUENCE DESCRIPTION: SEQ ID NO:9:

Gln Ser Val Gln Leu Gln Glu Ser Gly Pro Gly Leu Val Arg Pro Ser
1               5                   10                  15

Gln Thr Leu Ser Leu Thr Cys Thr Val Ser Gly Ser Thr Phe Ser Asp
                20                  25                  30

Phe Tyr Met Asn Trp Val Arg Gln Pro Pro Gly Arg Gly Leu Glu Trp
            35                  40                  45

Ile Gly Phe Ile Arg Asp Lys Ala Lys Gly Tyr Thr Thr Glu Tyr Asn
50                  55                  60

Pro Ser Val Lys Gly Arg Val Thr Met Leu Val Asp Thr Ser Lys Asn
65                  70                  75                  80

Gln Phe Ser Leu Arg Leu Ser Ser Val Thr Ala Ala Asp Thr Ala Val
                85                  90                  95

Tyr Tyr Cys Ala Arg Glu Gly His Thr Ala Ala Pro Phe Asp Tyr Trp
            100                 105                 110

Gly Gln Gly Ser Leu Val Thr Val Ser Ser
            115                 120

(2) INFORMATION FOR SEQ ID NO:10:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO:10:

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
                20                  25                  30

Leu Asn Trp Tyr Gln Gln Lys Pro Gly Lys Ala Pro Lys Leu Leu Ile
            35                  40                  45

Tyr Asn Thr Asn Asn Leu Gln Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys Arg
            100                 105

(2) INFORMATION FOR SEQ ID NO:11:

(i) SEQUENCE CHARACTERISTICS:
        (A) LENGTH: 331 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
GACATCAAGA TGACCCAGTC TCCCTCATTC CTGTCTGCAT CTGTGGGAGA CAGAGTCACT      60
CTCAACTGCA AAGCAAGTCA GAATATTGAC AAATACTTAA ACTGGTATCA GCAAAAGCTT     120
GGAGAATCTC CCAAACTCCT GATATATAAT ACAAACAATT TGCAAACGGG CATCCCATCA     180
AGGTTCAGTG GCAGTGGATC TGGTACTGAT TTCACACTCA CCATCAGCAG CCTGCAGCCT     240
GCAGCCTGAA GATGTTGCCA CATATTTCTG CTTGCAGCAT ATAAGTAGGC CGCGCACGTT     300
TGGAACTGGG ACCAAGCTGG AGCTGAAACG G                                    331
```

(2) INFORMATION FOR SEQ ID NO:12:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
GAGGTGAAAC TGTTGGAATC TGGAGGAGGC TTGGTACAGC CGGGGGGTTC TATGAGACTC      60
TCCTGTGCAG GTTCTGGATT CACCTTCACT GATTTCTACA TGAACTGGAT CCGCCAGCCT     120
GCAGGGAAGG CACCTGAGTG GCTGGGTTTT ATTAGAGACA AAGCTAAAGG TTACACAACA     180
GAGTACAATC CATCTGTGAA GGGGCGGTTC ACCATCTCCA GAGATAATAC CAAAACATG      240
CTCTATCTTC AAATGAACAC CCTAAGAGCT GAGGACACTG CCACTTACTA CTGTGCAAGA     300
GAGGGCCACA CTGCTGCTCC TTTTGATTAC TGGGGCCAAG GAGTCATGGT CACAGTCTCC     360
TCA                                                                   363
```

(2) INFORMATION FOR SEQ ID NO:13:

(i) SEQUENCE CHARACTERISTICS:
        (A) LENGTH: 367 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
CCAGGTCCAA CTGCAGGAGA GCGGTCCAGG TCTTGTGAGA CCTAGCCAGA CCCTGAGCCT      60
GACCTGCACC GTGTCTGGCA GCACCTTCAG CGATTTCTAC ATGAACTGGG TGAGACAGCC     120
ACCTGGACGA GGTCTTGAGT GGATTGGATT TATTAGAGAC AAAGCTAAAG GTTACACAAC     180
AGAGTACAAT CCATCTGTGA AGGGGAGAGT GACAATGCTG GTAGACACCA GCAAGAACCA     240
GTTCAGCCTG AGACTCAGCA GCGTGACAGC CGCCGACACC GCGGTCTATT ATTGTGCAAG     300
AGAGGGCCAC ACTGCTGCTC CTTTTGATTA CTGGGGTCAA GGCAGCCTCG TCACAGTCTC     360
CTCAGGT                                                               367
```

(2) INFORMATION FOR SEQ ID NO:14:

(i) SEQUENCE CHARACTERISTICS:
  (A) LENGTH: 340 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:14:

```
GACATCCAGA TGACCCAGAG CCCAAGCAGC CTGAGCGCCA GCGTGGGTGA CAGAGTGACC    60
ATCACCTGTA AAGCAAGTCA GAATATTGAC AAATACTTAA ACTGGTACCA GCAGAAGCCA   120
GGTAAGGCTC CAAAGCTGCT GATCTACAAT ACAAACAATT TGCAAACGGG TGTGCCAAGC   180
AGATTCAGCG GTAGCGGTAG CGGTACCGAC TTCACCTTCA CCATACAGCA GCCTCCAGCC   240
AGAGGACATC GCCACCTACT ACTGCTTGCA GCATATAAGT AGGCCGCGCA CGTTCGGCCA   300
AGGGACCAAG GTGGAAATCA AACGTGAGTA GAATTTAAAC                         340
```

(2) INFORMATION FOR SEQ ID NO:15:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:15:

```
GGCCAGTGGA TAGAC                                                    15
```

(2) INFORMATION FOR SEQ ID NO:16:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:16:

```
CAGTTTCATC TAGAACTGGA TA                                            22
```

(2) INFORMATION FOR SEQ ID NO:17:

(i) SEQUENCE CHARACTERISTICS:
  (A) LENGTH: 25 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:17:

```
GCAGTTGGGT CTAGAAGTGG ACACC                                         25
```

(2) INFORMATION FOR SEQ ID NO:18:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:18:

TCAGCTGAGT CGACTGTGAC                                                    20

(2) INFORMATION FOR SEQ ID NO:19:

(i) SEQUENCE CHARACTERISTICS:
                 (A) LENGTH: 20 base pairs
                 (B) TYPE: nucleic acid
                 (C) STRANDEDNESS: single
                 (D) TOPOLOGY: linear (ii) MOLECULE TYPE: DNA (genomic)

(xi) SEQUENCE DESCRIPTION: SEQ ID NO:19:

TCACCTGAGT CGACTGTGAC                                                    20

(2) INFORMATION FOR SEQ ID NO:20:

(i) SEQUENCE CHARACTERISTICS:
                 (A) LENGTH: 24 base pairs
                 (B) TYPE: nucleic acid
                 (C) STRANDEDNESS: single
                 (D) TOPOLOGY: linear (ii) MOLECULE TYPE: DNA (genomic)

(xi) SEQUENCE DESCRIPTION: SEQ ID NO:20:

AGTTTCACCT CGGAGTGGAC ACCT                                               24

(2) INFORMATION FOR SEQ ID NO:21:

(i) SEQUENCE CHARACTERISTICS:
                 (A) LENGTH: 20 base pairs
                 (B) TYPE: nucleic acid
                 (C) STRANDEDNESS: single
                 (D) TOPOLOGY: linear (ii) MOLECULE TYPE: DNA (genomic)

(xi) SEQUENCE DESCRIPTION: SEQ ID NO:21:

TCACCTGAGG AGACTGTGAC                                                    20

(2) INFORMATION FOR SEQ ID NO:22:

(i) SEQUENCE CHARACTERISTICS:
                 (A) LENGTH: 17 base pairs
                 (B) TYPE: nucleic acid
                 (C) STRANDEDNESS: single
                 (D) TOPOLOGY: linear (ii) MOLECULE TYPE: DNA (genomic)

(xi) SEQUENCE DESCRIPTION: SEQ ID NO:22:

GGCTGGCGAA TCCAGTT                                                       17

(2) INFORMATION FOR SEQ ID NO:23:

(i) SEQUENCE CHARACTERISTICS:
                 (A) LENGTH: 39 base pairs
                 (B) TYPE: nucleic acid
                 (C) STRANDEDNESS: single
                 (D) TOPOLOGY: linear (ii) MOLECULE TYPE: DNA (genomic)

(xi) SEQUENCE DESCRIPTION: SEQ ID NO:23:

CTGTCTCACC CAGTTCATGT AGAAATCGCT GAAGGTGCT        39

(2) INFORMATION FOR SEQ ID NO:24:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CATTGTCACT CTCCCCTTCA CAGATGGATT GTACTCTGTT GTGTAACCTT TAGCTTTGTC        60

TCTAATAAAT CCAATCCACT C        81

(2) INFORMATION FOR SEQ ID NO:25:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GCCTTGACCC CAGTAATCAA AAGGAGCAGC AGTGTGGCCC TCTCTTGCAC AATA        54

(2) INFORMATION FOR SEQ ID NO:26:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

AGAAATCGST GAAGGTGAAG CCAGACA        27

(2) INFORMATION FOR SEQ ID NO:27:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

TGCAGCATCA GCC        13

(2) INFORMATION FOR SEQ ID NO:28:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

CTGCTGGTAC CAGTTTAAGT ATTTGTCAAT ATTCTGACTT GCTTTACAGG TGATGGT        57

(2) INFORMATION FOR SEQ ID NO:29:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
GCTTGGCACA CCCGTTTGCA AATTGTTTGT ATTGTAGATC AGCAG          45
```

(2) INFORMATION FOR SEQ ID NO:30:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
CCCTTGGCCG AACGTGCGCG GCCTACTTAT ATGCTGCAAG CAGTAGTAGG T    51
```

(2) INFORMATION FOR SEQ ID NO:31:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

```
CTGCAGACAT CCAGATGACC CAGAGCCCAA GCAGCCTGAG CGCCAGCGTG GGTGACAGAG     60

TGACCATCAC CTGTAGAGCC AGCGGTAACA TCCACAACTA CCTGGCTTGG TACCAGCAGA    120

AGCCAGGTAA GGCTCCAAAG CTGCTGATCT ACTACACCAC CACCCTGGCT GACGGTGTGC    180

CAAGCAGATT CAGCGGTAGC GGTAGCGGTA CCGACTTCAC CTTCACCATC AGCAGCCTCC    240

AGCCAGAGGA CATCGCCACC TACTACTGCC AGCACTTCTG GAGCACCCCA AGGACGTTCG    300

GCCAAGGGAC CAAGGTGGAA ATCAAACGTG AGTAGAATTT AAACTTTGCT TCCTCAGTTG    360

GATCCTAGAA TTC                                                      373
```

(2) INFORMATION FOR SEQ ID NO:32:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO:32:

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Asn Ile His Asn Tyr
                20                  25                  30

Leu Ala Trp Tyr Gln Gln Lys Pro Gly Lys Ala Pro Lys Leu Leu Ile
            35                  40                  45

Tyr Tyr Thr Thr Thr Leu Ala Asp Gly Val Pro Ser Arg Phe Ser Gly
```

```
                50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln His Phe Trp Ser Thr Pro Arg
                 85                  90                  95

Thr Phe Gly Gln Gly Thr Lys Val Glu Ile Lys Arg
                100                 105
```

(2) INFORMATION FOR SEQ ID NO:33:

(i) SEQUENCE CHARACTERISTICS:
        (A) LENGTH: 614 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

```
ATGCAATCCT CTGAATCTAC ATGGTAAATA TAGGTTTGTC TATACCACAA ACAGAAAAAC    60

ATGAGATCAC AGTTCTCTCT ACAGTTACTG AGCACACAGG ACCTCACCAT GGGATGGAGC   120

TGTATCATCC TCTTCTTGGT AGCAACAGCT ACAGGTAAGG GGCTCACAGT AGCAGGCTTG   180

AGGTCTGGAC ATATATATGG GTGACAATGA CATCCACTTT GCCTTTCTCT CCACAGGTGT   240

CCACTCCGAC ATCCAGATGA CCCAGAGCCC AAGCAGCCTG AGCGCCAGCG TGGGTGACAG   300

AGTGACCATC ACCTGTAGAG CCAGCGGTAA CATCCACAAC TACCTGGCTT GGTACCAGCA   360

GAAGCCAGGT AAGGCTCCAA AGCTGCTGAT CTACTACACC ACCACCCTGG CTGACGGTGT   420

GCCAAGCAGA TTCAGCGGTA GCGGTAGCGG TACCGACTTC ACCTTCACCA TCAGCAGCCT   480

CCAGCCAGAG GACATCGCCA CCTACTACTG CCAGCACTTC TGGAGCACCC CAAGGACGTT   540

CGGCCAAGGG ACCAAGGTGG AAATCAAACG TAGTAGAATT TAAACTTTGC TTCCTCAGTT   600

GGATCCTAGA ATTC                                                    614
```

(2) INFORMATION FOR SEQ ID NO:34:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO:34:

```
Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Ala Ser Gly Asn Ile
             35                  40                  45

His Asn Tyr Leu Ala Trp Tyr Gln Gln Lys Pro Gly Lys Ala Pro Lys
         50                  55                  60

Leu Leu Ile Tyr Tyr Thr Thr Thr Leu Ala Asp Gly Val Pro Ser Arg
 65                  70                  75                  80

Phe Ser Gly Ser Gly Ser Gly Thr Asp Phe Thr Phe Thr Ile Ser Ser
                 85                  90                  95

Leu Gln Pro Glu Asp Ile Ala Thr Tyr Tyr Cys Gln His Phe Trp Ser
                100                 105                 110
```

```
Thr Pro Arg Thr Phe Gly Gln Gly Thr Lys Val Glu Ile Lys Arg
        115                 120                 125
```

(2) INFORMATION FOR SEQ ID NO:35:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

```
GACATCCAGA TGACCCAGAG CCCAAGCAGC CTGAGCGCCA GCGTGGGT                    48
```

(2) INFORMATION FOR SEQ ID NO:36:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

```
GACAGAGTGA CCATCACCTG TAGAGCCAGC GGTAACATCC ACAACTACCT                  50

GGCTTGGTAC                                                              60
```

(2) INFORMATION FOR SEQ ID NO:37:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

```
CAAGCCAGGT AGTTGTGGAT GTTACCGCTG GCTCTACAGG TGAT                        44
```

(2) INFORMATION FOR SEQ ID NO:38:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

```
GGTCACTCTG TCACCCACGC TGGCGCTCAG GCT                                    33
```

(2) INFORMATION FOR SEQ ID NO:39:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

```
GCTTGGGCTC TGGGTCATCT GGATGTCTGC A                                      31
```

(2) INFORMATION FOR SEQ ID NO:40:

(i) SEQUENCE CHARACTERISTICS:
      (A) LENGTH: 49 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:40:

CAGCAGAAGC CAGGTAAGGC TCCAAAGCTG CTGATCTACT ACACCACCA          49

(2) INFORMATION FOR SEQ ID NO:41:

(i) SEQUENCE CHARACTERISTICS:
      (A) LENGTH: 49 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:41:

CCCTGGCTGA CGGTGTGCCA AGCAGATTCA GCGGTAGCGG TAGCGGTAC          49

(2) INFORMATION FOR SEQ ID NO:42:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:42:

CGCTACCGCT ACCGCTGAAT CTGCT                                    25

(2) INFORMATION FOR SEQ ID NO:43:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:43:

TGGCACACCG TCAGCCAGGG TGGTGGTGTA GTAGATCAGC                    40

(2) INFORMATION FOR SEQ ID NO:44:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:44:

AGCTTTGGAG CCTTACCTGG CTTCTGCTGG TAC                           33

(2) INFORMATION FOR SEQ ID NO:45:

```
    (i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

CGACTTCACC TTCACCATCA GCAGCCTCCA GCCAGAGGAC ATCGCCACCT ACTACTGCC          59

(2) INFORMATION FOR SEQ ID NO:46:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

AGCACTTCTG GAGCACCCCA AGGACGTTCG GCCAAGGGAC CAAGGTGGA                    49

(2) INFORMATION FOR SEQ ID NO:47:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

AATCAAACGT GAGTAGAATT TAAACTTTGC TTCCTCAGTT GGATCCTAG                    49

(2) INFORMATION FOR SEQ ID NO:48:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

AATTCTAGGA TCCAACTGAG GAAGCAAAGT TTAAA                                   35

(2) INFORMATION FOR SEQ ID NO:49:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

TTCTACTCAC GTTTGATTTC CACCTTGGTC CCTT                                    34

(2) INFORMATION FOR SEQ ID NO:50:

(i) SEQUENCE CHARACTERISTICS:
        (A) LENGTH: 44 base pairs
        (B) TYPE: nucleic acid
        (C) STRANDEDNESS: single
```

-continued

```
          (D) TOPOLOGY: linear (ii) MOLECULE TYPE: DNA (genomic)

(xi) SEQUENCE DESCRIPTION: SEQ ID NO:50:

GGCCGAACGT CCTTGGGGTG CTCCAGAAGT GCTGGCAGTA GTAG               44

(2) INFORMATION FOR SEQ ID NO:51:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:51:

CTGGCGATGT CCTCTGGCTG GAGGCT                                   26

(2) INFORMATION FOR SEQ ID NO:52:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:52:

GCTGATGGTG AAGGTGAAGT CGGTAC                                   26

(2) INFORMATION FOR SEQ ID NO:53:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:53:

TCATCTGGAT GTCGGAGTGG ACACCT                                   26
```